United States Patent
Ratain et al.

(10) Patent No.: US 7,807,350 B2
(45) Date of Patent: Oct. 5, 2010

(54) METHODS FOR PREDICTING IRINOTECAN TOXICITY

(75) Inventors: Mark J. Ratain, Chicago, IL (US);
Federico Innocenti, Chicago, IL (US);
Anna Di Rienzo, Chicago, IL (US);
Carrie Grimsley, Kankakee, IL (US)

(73) Assignee: The University of Chicago, Chicago, IL (US)

(*) Notice: Subject to any disclaimer, the term of this patent is extended or adjusted under 35 U.S.C. 154(b) by 673 days.

(21) Appl. No.: 10/558,510

(22) PCT Filed: May 28, 2004

(86) PCT No.: PCT/US2004/016920

§ 371 (c)(1),
(2), (4) Date: Oct. 23, 2006

(87) PCT Pub. No.: WO2004/108954

PCT Pub. Date: Dec. 16, 2004

(65) Prior Publication Data

US 2007/0197574 A1    Aug. 23, 2007

Related U.S. Application Data

(60) Provisional application No. 60/474,826, filed on May 30, 2003.

(51) Int. Cl.
*C12Q 1/68* (2006.01)
*C12P 19/34* (2006.01)
*C07H 21/04* (2006.01)
*A61K 31/44* (2006.01)

(52) U.S. Cl. ............ 435/6; 435/91.2; 536/25.32; 514/283

(58) Field of Classification Search .......... None
See application file for complete search history.

(56) References Cited

U.S. PATENT DOCUMENTS

| | | | |
|---|---|---|---|
| 5,786,344 A | 7/1998 | Ratain et al. | 514/100 |
| 5,972,614 A | 10/1999 | Ruano et al. | 435/6 |
| 6,066,645 A | 5/2000 | Hausheer et al. | 514/283 |
| 6,287,834 B1 | 9/2001 | Belanger et al. | 435/193 |
| 6,319,678 B1 | 11/2001 | Trubetskoy et al. | 435/15 |
| 6,395,481 B1 | 5/2002 | Di Rienzo et al. | 435/6 |
| 6,407,117 B1 | 6/2002 | Bouscarel et al. | 514/283 |
| 6,448,003 B1 | 9/2002 | Guida et al. | 435/6 |
| 6,472,157 B1 | 10/2002 | Di Rienzo et al. | 435/6 |
| 6,479,236 B2 | 11/2002 | Penny et al. | 435/6 |
| 6,586,175 B1 | 7/2003 | Galvin et al. | 435/6 |
| 2002/0061518 A1 | 5/2002 | Penny et al. | 435/6 |
| 2003/0077629 A1 | 4/2003 | Galvin et al. | 435/6 |
| 2003/0099960 A1 | 5/2003 | Ratain et al. | 435/6 |
| 2003/0099977 A1 | 5/2003 | Guida et al. | 435/6 |
| 2003/0157517 A1 | 8/2003 | Penny et al. | 435/6 |
| 2004/0058363 A1 | 3/2004 | Hasegawa et al. | 435/6 |
| 2004/0076968 A1 | 4/2004 | Acuna et al. | 435/6 |
| 2004/0121327 A1 | 6/2004 | Manns et al. | 435/6 |
| 2004/0203034 A1 | 10/2004 | Ratain et al. | 435/6 |

FOREIGN PATENT DOCUMENTS

| | | |
|---|---|---|
| EP | 0919244 | 6/1999 |
| EP | 1352970 | 10/2003 |
| JP | 2004-073035 | 3/2004 |
| WO | WO 94/22846 | 10/1994 |
| WO | WO 95/08986 | 4/1995 |
| WO | WO 96/01127 | 1/1996 |
| WO | WO 97/32042 | 9/1997 |
| WO | WO 99/57322 | 11/1999 |
| WO | WO 00/06776 | 2/2000 |
| WO | WO 01/79230 | 10/2001 |
| WO | WO 02/06523 | 1/2002 |
| WO | WO 02/053770 | 7/2002 |
| WO | WO 02/057410 | 7/2002 |
| WO | WO 03/013536 | 2/2003 |
| WO | WO 03/013537 | 2/2003 |
| WO | WO 2004/016814 | 2/2004 |

OTHER PUBLICATIONS

Ruano, G. et al. Nucleic Acids Research 19(24):6877-6882 (1991).*
Abraham et al., "Non-glucocorticoid steriod analogues (21-aminosteroids) sensitize multidrug resistant cells to vinblastine," *Cancer Chemother. Pharmacol.*, 32(2):116-122, 1993.
Akiyama et al., "Most drugs that reverse multidrug resistance also inhibit photoaffinity labeling of p-glycoprotein by a vinblastine analog," *Mol. Pharmacol.*, 33(2):144-147, 1988.
Ando et al., "Polymorphisms of UDP-Glucuronsyltransferase Gene and Irinotecan Toxicity: A Pharmacogenetic Analysis," *Cancer Res.*, 60(24):6921-6926, 2000.
Ando et al., "UGT1A1 genotypes and glucuronidation of SN-38, the active metabolite of irinotecan," *Annals of Oncology*, 9:845-847, 1998.
Ansher et al., "Chemoprotective effects of two dithiolthiones and of butylhydroxyanisole against carbon tetrachloride and acetaminophen toxicity," *Hepatology*, 3(6):932-935, 1983.
Araki et al., "Relationship between development of diarrhea and the concentration of SN-38, an active metabolite of CPT-11, in the intestine and blood plasma of athymic mice following intraperitoneal administration of CPT-11," *Jpn J. Cancer Res.*, 84:697-702, 1993.
Ariyoshi et al., "Mouse-human chimeric antibody MH171 against the multidrug transporter P-glycoprotein," *Jpn. J. Cancer Res.*, 83(5):515-521, 1992.
Atsumi et al., "Identification of the Metabolites of Irinotecan, a New Derivative of Camptothecin, in Rat Bile and its Biliary Excretion," *Xenobiotica*, 21(9):1159-1169, 1991.

(Continued)

*Primary Examiner*—Diana B Johannsen
(74) *Attorney, Agent, or Firm*—Fulbright & Jaworski L.L.P.

(57) ABSTRACT

The present invention concerns the methods and compositions for evaluating the risk of ironotecan toxicity in a cancer patient based on the genotype of the patient at position −3156 of the UGT1A1 gene or at any position in linkage disequilibrium with the −3156 variant.

14 Claims, 6 Drawing Sheets

OTHER PUBLICATIONS

Barbier et al., "3'-azido-3'-deoxythimidine (AZT) is glucuronidated by human UDP-glucuronosyltransferase 3B7 (UGT2B7)," *Drug Metab. Dispos.*, 28:497-502, 2000.

Barker et al., "Determination of plasma concentrations of epirubicin and its metabolites by high-performance liquid chromatography during a 96-h infusion in cancer chemotherapy," *J Chromatogr B Biomed Appl*, 681:323-329, 1996.

Bear, "Drugs transported by-P-glycoprotein inhibit a 40pS outwardly rectifying chloride channel," *Biochem. Biophys. Res. Commun.*, 200(1):513-521, 1994.

Bell et al., "Roles of peptidyl-prolyl cis-trans isomerase and calcineurin in the mechanisms of antimalarial action of cyclosporin A, FK506, and rapamycin," *Biochem. Pharmacol.*, 48(3):495-503, 1994.

Bertrand et al.., "Sequential Administration of Camptothecin and Etoposide Circumvents the Antagonistic Cytotoxicity of Simultaneous Drug Administration in Slowly Growing Human Colon Carcinoma HT-29 Cells," *Eur. J. Cancer*, 28A(4-5):743-748, 1992.

Beutler et al., "Racial variability in the UDP-glucuronosyltransferase 1 (UGT1A1) promoter: a balanced polymorphism for regulation of bilirubin metabolism," *PNAS USA*, 95:8170-8174, 1998.

Bhasker et al., "Genetic polymorphism of UDP-glucuronosyltransferase 2B7 (UGT2B7) at amino acid 268: ethnic diversity of alleles and potential clinical significance," *Pharmacogenetics*, 10(8):679-685, 2000.

Bible and Kaufmann, "Cytotoxic synergy between flavopiridol (NSSC 649890, L86-8275) and various antineoplastic agents: the importance of sequence of administration," *Cancer Res.*, 57:3375-3380, 1997.

Bible and Kaufmann, "Flavopiridol: a cytotoxic flavone that induces cell death in noncycling A549 human lung carcinoma cells," *Cancer Res.*, 56:4856-4861, 1996.

Bock et al., "Purification of Rat Liver UDP-Glucuaronyltransferase: Separation of Two Enzyme Forms with Different Substrate Specificity and Differential Inducibility," In: Conjugation reactions in biotransformation, Elsevier, North Holland Biomedical Press, p. 357-364, 1978.

Boesch and Loor, "Extent and persistence of P-glycoprotein inhibition in multidrug-resistant P388 cells after exposure to resistance-modifying agents," *Anticancer Drugs*, 5(2):229-238, 1994.

Boesch et al., "Restoration of daunomycin retention in multidrug-resistant P388 cells by submicromolar concentrations of SDZ PSC 833, a nonimmunosuppressive cyclosporin derivative," *Exp. Cell. Res.*, 196(1):26-32, 1991.

Boiteux-Antoine et al., "Comparative induction of drug-metabolizing enzymes by hypolipidaemic compounds," *Gen-Pharmacol*, 20(4):407-412, 1989.

Bosma et al., "Sequence of exons and the flanking regions of human bilirubin-UDP-glucuronosyltransferase gene complex and identification of a genetic mutation in a patient with Crigler-Najjar Syndrome, Type I," *Hepatology*, 15:941-947, 1992.

Bosma et al., "The genetic basis of the reduced expression of bilirubin UDP-glucuronosyltransferase 1 in Gilbert's syndrome," *New England Journal of Medicine*, 333:1171-1175, 1995.

Burchell and Coughtrie, "UDP-glucuronosyltransferases," *Pharmac. Ther.*, 43:261-289, 1989.

Burchell et al., "The UDP Glucuronosyltransferase gene suprefamily: suggested nomenclature based on evolutionary divergence," *DNA Cell Biol.*, 10:487-494, 1991.

Burger et al., "Pharmacokinetic interaction between rifampin and zidovudine," *Antimicrobial Agents and Chemotherapy*, 37(7):1426-1431, 1993.

Campain et al., "Characterization of an unusual mutant of human melanoma cells resistant to anticancer drugs that inhibit topoisomerase II," *J. Cell Physiol.*, 155(2):414-425, 1993.

Carlson et al., "Flavopiridol induces G[1] arrest with inhibition of cyclin-dependent kinase (CDK) 2 and CDK4 in human breast carcinoma cells," *Cancer Res*, 56:2973-2978, 1996.

Carrier et al., "Isolation and characterization of the human UGT2B7 gene," *Biochem and Biophys. Res. Commun.*, 272:616-621, 2000.

Cascorbi et al., "Frequency of single nucleotide polymorphisms in the p-glycoprotein drug transporter MDR1 gene in white subjects," *Clinc. Pharmacol Ther.*, 69:169-174, 2001.

Charuk et al., "Interaction of Rat Kidney P-Glycoprotein with a Urinary Component and Various Drugs Including Cyclosporin A," *Am. J. Physiol.*, 266:F66-F75, 1994.

Chen and Okayama, "Calcium phosphate-mediated gene transfer: A highly efficient transfection system for stably transforming cells with plasmid DNA," *Biotechniques*, 6:632-638, 1988.

Chen et al., "Fluorescence polarization in homogeneous nucleic acid analysis," *Genome Res.*, 9:492-498, 1999.

Cheng et al., "Glucuronidation of catechol estrogens by expressed human UDP-glucuronosyltransferases (UGTs) 1A1, 1A3, and 2B7," *Toxicological Sciences*, 45:52-57, 1998.

Chien et al., "In vitro evaluation of flavopiridol, a novel cell cycle inhibitor, in bladder cancer," *Cancer Chemother Pharmacol.*, 44:81-87, 1999.

Chin et al., "Reduced mRNA levels for multidrug-resistance genes in cAMP-dependent protein kinase mutant cell lines," *J. Cell Physiol.*, 152(1):87-94, 1992.

Clarke et al., "Genetic defects of the UDG-glucuronosyltransferase-1 (UGT1) gene that cause familial non-haemolytic unconjugated hyperbilirubinaemias," *Clinca Chimica Acata*, 266:63-74, 1997.

Clarke et al., "The Uridine Diphosphate glucuronosyltransferase multigene family: function and regulation," *Handbook of Experimental Pharmacology*, 112:3-43, 1994.

Coffman et al., "Cloning and stable expression of a cDNA encoding a rate liver UDP-Glucuronosyltransferase (UDP_Glucuronosyltransferase 1.1) that catalyzes the glucuronidation of opiods and bilirubin," *Mol. Pharmacol.*, 47:1101-1105, 1995.

Coffman et al., "Human UGT2B7 catalyzes morphine glucuronidation," *Drug Metab Dispos.*, 25:1-4, 1997.

Coffman et al., "The glucuronidation of opioids, other xenobiotics, and androgens by human UGT2B7Y(268) and UGT2B7H(268)," *Drug Metab Dispos*, 26:73-77, 1998.

Cordon-Cardo et al., "Expression of the multidrug resistant gene product (P-glycoprotein) in human normal and tumor tissues," *J. Histochem. Cytochem.*, 38:1277-1287, 1990.

Czech et al., "Antitumoral activity of flavone L86-8275," *Int J Oncol*, 6:31-66, 1995.

Davies and Schnell, "Oltipraz-induced amelioration of acetaminophen hepatotoxicity in hamseters," *Toxicology and Applied Pharmacology*, 109:29-40, 1991.

de Forni et al., "Phase I and pharmacokinetic study of the camptothecin derivative irinotecan administered on a weekly schedule in cancer patients," *Cancer Res.*, 54:4347-4354, 1994.

De Lannoy et al., "Cyclosporin and Quinidine Inhibition of Renal Digoxin Excretion: Evidence for Luminal Secretion of Digoxin," *Am. J. Physiol*, 263:F613-F622, 1992.

De Morais et al., "Biotransformation and Toxicity of Acetaminophen in Congenic RHA Rats with or without a Hereditary Deficiency in Bilirubin UDP-Glucuronosyltransferase," *Toxicology and Applied Pharmacology*, 117:81-87, 1992.

De Morais et al., "Decreased Glucuronidation and Increased Bioactivation of Acetaminophen in Gilbert's Syndrome," *Gastroenterology*, 102:577-580, 1992.

Decleves et al., "A new polymorphism (N21D) in the exon 2 of the human MDRI gene encloding the P-glycoprotein," *Human Mutation*, Mutation and Polymorhism Report #115, 2000.

Dhainaut et al., "New Triazine Derivatives as Potent Modulators of Multidrug Resistance," *J. Med. Chem.*, 35:2481-2496, 1992.

Di Carlo et al., "Flavonoids: old and new aspects of a class of natural therapeutic drugs," *Life Sci*, 65:337-353, 1999.

Di Rienzo et al., "Two new alleles in the promoter of the bilirubin UDP-glucuronosyl transferase 1 (UGT1A1) gene", *American Society for Clinical Pharmacology and Therapeutics*, Ninety Ninth Annual Meeting, New Orleans, Abstract OII-B-3, p. 207, 1998.

Diasio and Harris, "Clinical pharmacology of 5-fluorouracil," *Clin Pharmacokinet*, 16:215-237, 1989.

Dobbs and Twelves, "What is the effect of adjusting epirubicin doses for body surface area?" *British Journal of Cancer*, 78(5):662-666, 1998.

Doige et al., "ATPase activity of partially purified P-glycoprotein from multidrug-resistant chinese hamster ovary cells," *Biochim. Biophys. Acta.*, 1109(2):149-160, 1992.

Drees et al., "Flavopiridol (86-8275): selective antitumor activity in vitro and activity in vivo for prostate carcinoma cells," *Clin Cancer Res*, 3:273-279, 1997.

Egner et al., "Regulation of Phase 2 Enzyme Induction by Oltipraz and other Dithiolethiones," *Carcinogenesis*, 15(2):177-181, 1994.

Evans and Relling, "Automated high-performance liquid chromatographic assay for the determination of 7-ethoxycoumarin and umbelliferone," *J. Chromatography*, 578:141-145, 1992.

Ford et al., "Cellular and biochemical characterization of thioxanthenes for reversal of multidrug resistance in human and murine cell lines," *Cancer Res.*, 50(6):1748-1756, 1990.

Fournel et al., "Structure-dependent induction of bilirubin glucuronidation and lauric acid 12-hydroxylation by arylcarboxylic acids chemically related to clofibrate," *Biochimica at Biophysica Acta*, 842:202-213, 1985.

Foxwell et al., "Identification of the multidrug resistance-related P-glycoprotein as a cyclosporine binding protein," *Mol. Pharmacol.*, 36:543-546, 1989.

Friche et. al., "In vitro circumvention of anthracycline-resistance in ehrlich ascites tumour by anthracycline analogues" *Biochem. Pharmacol.*, 39:1721-1726, 1990.

Gestl et al., "Expression of UGT2B7, a UDP-glucuronosyltransferase implicated in the metabolism of 4-hydroxyestrone and all-trans retinoic acid, in normal human breast parenchyma and in invasive and in Situ breast cancers," *American Journal of Pathology*, 160(4):1467-1479, 2002.

Gram et al., "Clinical relevance of gentic polymorphisms in drug oxidation," *Clinical Relevance of Genetic Polymorphisms in Drug Oxidation*, 1992.

Green et al., "Expressed human UGT1.4 protein catalyzes the formation of quaternary ammonium-linked glucuronides," *Drug Metab. Dispos.*, 23:299-302, 1995.

Gruol et al., "Reversal of multidrug resistance by RU 486[1]," *Cancer Res.*, 54(12):3088-3091, 1994.

Gunn, "Hereditary Acholuric Jaundice," *J. Hered.*, 29:137-139, 1938.

Gupta et al., "Metabolic Fate of Irinotecan in humans: Correlation of Glucuronidation with Diarrhea," *Cancer Res.*, 54:3723-3725, 1994.

Gupta et al., "Pharmacokinetic and pharmacodynamic evaluation of the topisomerase inhibitor Irinotecan in cancer patients," *J. Clin. Oncol.*, 15:1502-1510, 1997.

Gupta et al., "Role of carboxyl esterase in the metabolism of CPT-11, a camptothecin analog, in humans" *Pharm. Res.*, 11:S450, 1994.

Gutmann et al., "Modulation of multidrug resistance protein expression in porcine brain capillary endothelial cells in vitro," *Drug Metab Dispos.* 27:937-941, 1999.

Hait et al., "Terferadine (seldane®): a new drug for restoring sensitivity to multidrug resistant cancer cells," *Biochem. Pharmacol.*, 45(2):401-406, 1993.

Hamada et al., "Mouse-human chimeric antibody against the multidrug transporter P-glycoprotein," *Cancer Res.*, 50(11):3167-3171, 1990.

Harding et al., "Cloning and substrate specificity of a human phenol UDP-glucuronosyltransferase expressed in COS-7 cells," *PNAS, USA*, 85:8381-8385, 1988.

Hecht et al., "4-(Methylnitrosamino)-1-(3-pyridyl)-1-butanol (NNAL) and its glucuronide, metabolites of a tobacco-specific lung carcinogen, in the urine of black and white smokers," *Proceedings of the American Association for Cancer Research*, 35:1702, 1994.

Hendricks et al., "Effect of P-Glycoprotein Expression on the Accumulation and Cytotoxicity of Topotecan (SK&F 104864), a New Campotthecin Analogue," *Cancer Research*, 52:2268-2278, Apr. 1992.

Hjelle, "Hepatic UDP-Glucuronic Acid Regulation during Acetaminophen Biotransformation in Rats," *The Journal of Pharmacology and Experimental Therapeutics*, 237(3):750-756, 1986.

Hoffmeyer et al., "Functional polymorphisms of the human multidrug-resistance gene: multiple sequence variations an dcorrelation of one allele with p-glycoprotein expression and activity in vivo," *PNAS*, 28:97(7):3473-3478, 2000.

Holthe et al., "Morphine glucuronide-to-morphine plasma ratios are unaffected by the UGT2B7 H268Y and UGT1a1*28 polymorphisms in cancer patients on chronic morphine therapy," *European Journal of Clinical Pharmacology*, 58: 353-356, 2002.

Hooijberg et al., "Potent interaction of flavopiridol with MRP1," *British J. of Cancer*, 81:269-276, 1999.

Hsu et al., "Universal SNP genotyping assay with fluorescence polarization detection," *BioTechniques*, 31:560-570, 2001.

Hunter et al, "Drug absorption limited by P-glycoprotein-mediated secretory drug transport in human intestinal epithelial caco-2 cell layers," *Pharm. Res.*, 10(5):743-749, 1993.

Ichikawa-Haraguchi et al., "Progesterone and its metabolites: the potent inhibitors of the transporting activity of P-glycoprotein in the adrenal gland," *Biochim. Biophys. Acta*, 1158(3):201-208, 1993.

Innocenti et al., "Epirubicin glucuronidation is catalyzed by human UDP-glucuronosyl transferase 2B7," *Drug Metab. Dispos.*, 29(5):686-692, 2001.

Innocenti et al., "Epirubicin is glucuronidated by UGT2B7," *Clinical Pharmacology and Therapeutics*, 67(2):100, Abstract PI-44, 2000.

Innocenti et al., "Flavopiridol metabolism in cancer patients is associated with the occurrence of diarrhea," *Clinical Cancer Research*, 6:3400-3405, 2000.

Innocenti et al., "Genetic variants in the UDP-glucuronosyltransferase 1A1 gene predict the risk of severe neutropenia of irinotecan," *J. Clin. Oncol.*, 22:1382-1388, 2004.

Innocenti et al., "Haplotype structure of the UDP-glucuronosyltransferase 1A1 promoter in different ethnic groups," *Pharmacogenetics*, 12:725-733, 2002.

Innocenti et al., "Pharmacogenetics of Anticancer Agents: Lessons From Amonafide and Irinotecan," *Drug Metabolism and Disposition*, 29:596-600, 2001.

Inoue et al., "Cellular detoxification of tripeptidyl aldehydes by an aldo-keto reductase," *J. Biol. Chem.*, 268(8):5894-5898, 1993.

Ishii et al., "Octamer transcription factor-1 enhances hepatic nuclear factor-1 α-mediated activation of the human UDP glucuronosyltransferase 2B7 promoter," *Molecular Pharmacology*, 57:940-947, 2000.

Ito et al., "Polymorphism of the abc transporter genes mdr1, mrp1 and mrp2/cmoat, in healthy japanese subjects," *Pharmacogenetics*, 11:175-184, 2001.

Iyer and Ratain, "Pharmacogenetics and cancer chemotherapy," *Eur J Cancer*, 34:1493-1499, 1998.

Iyer et al., "Genetic basis for the glucuronidation of SN-38: Role of UGT*1 isoform," *Clinical Pharmacology and Therapeutics*, 61:Abstract, 1997.

Iyer et al., "Glucuronidation of TAS-103 by uridine diphosphate glucuronosyltransferase (UGT) isoforms 1a1 and 2: possible implication of TAS-103 toxicity in Gilbert's syndrome," *Ann Oncol* 9(Supplement 2):61, abstract #230, 1998.

Iyer et al., "UGT isoform 1.1 (UGT*1.1) glucuronidates SN-38, the active metabolite of irinotecan," *Program Proceedings of the American Society of Clinical Oncology*, 16:Abstract, 1997.

Iyer, "Inherited variations in drug-metabolizing enzymes: significance in clinical oncology," *Mol Diagnosis*, 4:327-333, 1999.

Jager et al., "Metabolism of the anticancer drug vlavopiridol, a new inhibitor of cyclin dependent kinases in rat liver," *Life Sci.*, 62:1861-1873, 1998.

Jin et al., "cDNA cloning and expression of two new members of the human glucuronosyltransferase 2B subfamily," *Biochem. Biphys. Res. Comm.*, 194(1):496-503, 1993.

Jin et al., "Complementary deoxyribonucleic acid cloning and expression of human liver uridine diphosphate-glucuronosyltransferase glucuronidating carboxylic acid-containing drugs," *J. Pharm. Experim. Therap.*, 264(1):475-479, 1993.

Kamimoto et al., "The function of GP-170, the multidrug resistant gene product, in rat liver canalicular membrane vesicles," *J. Biol. Chem.*, 264:11693-11698, 1989.

Kamiwatari et al., "Correlation between reversing of multidrug resistance and inhibiting of [$^3$H]azidopine photolabeling of P-glycoprotein by newly synthesized dihydrophyridine analogues in a human cell line," *Cancer Res.*, 49(12):3190-3195, 1989.

Kaneda et al., "Metabolism and Pharmacokinetics of the campothecin analogue CPT-11 in the mouse," *Cancer Res.*, 50:1715-1720, 1990.

Kano et al., "Effects of CPT-11 in Combination with Other Anti-Cancer Agents in Culture," *Int. J. Cancer*, 50(4):604-610, 1992.

Karato et al., "Phase I Study of CPT-11 and Etoposide in Patients with Refractory Solid Tumors," *J. Clin. Oncol.*, 11(10):2030-2035, 1993.

Kaufmann, "Antagonism Between Camptothecin and Topoisomerase II-Directed Chemotherapeutic Agents in a Human Leukemia Cell Line," *Cancer Res.*, 51(4):1129-1136, 1991.

Kaur et al., "Growth inhibition with reversible cell cycle arrest of carcinoma cells by flavone L86-8275," *J Natl Cancer Inst.*, 84:1736-1740, 1992.

King et al., "The Glucuronidation of exogenous and endogenous compounds by stably expressed rat and human UDP-Glucuronosyltransferase 1.1," *Arch. Biochem. Biophys.*, 332:92-100, 1996.

Kiue et al., "Activities of newly synthesized dihydropyridines in overcoming of vincristine resistance, calcium antagonism, and inhibition of photoaffinity labeling of P-glycoprotein in rodents," *Cancer Res.*, 50(2):310-317, 1990.

Klein et al., "An inventory of the human ABC proteins," *Bioch Biophys Acta*, 1461:237-262, 1999.

Kusuhara et al., "Reduced folate derivatives are endogenous substrates for cmoat in rats," *Am J Physiol.*, 275(4 Pt 1):G789-G796, 1998.

Lampe et al., "Prevalence of polymorphisms in the human UDP-glucuronosyltransferase 2B family: UGT2B4(D458E), UGT2B7(H268Y), and UGT2B15(D85Y)," *Cancer Epidemiology, Biomarkers and Prevention, American Association for Cancer Research*, 9:329-333, 2000.

Lennard et al., "Pharmacogenetics of acute azathioprine toxicity: relationship to thiopurine methyltransferase genetic polymorphism," *Clin. Pharmacol. Ther.*, 46:149-154, 1989.

Lennard, "The clinical pharmacology of 6-mercaptopurine," *Eur J Clin Pharmacol*, 43:329-339, 1992.

Levesque et al., "Characterization and substrate specificity of UGT2B4 (E $^{458}$) a udp-glucuronosyltransferase encoded by a polymorphic gene," *Pharmacogenetics*, 9:207-216, 1999.

Levesque et al., "Isolation and characterization of UGT2B15($Y^{85}$): a UDP-glucuronosyltransferase encoded by a polymorphic gene," *Pharmacogenetics*, 7:317-325, 1997.

Lokiec et al., "Pharmacokinetics of irinotecan and its metabolites in human blood, bile and urine," *Cancer Chemother. Pharmacol.*, 36:79-82, 1995.

Lomri et al., "Hepatocellular transport: role of atp-binding cassette proteins," *Semin. Liv. Dis.*, 16: 201-210, 1996.

Losiewicz et al., "Potent inhibition of CDC2 kinase activity by the flavonoid L86-8275," *Biochem Biophys Res Commun*, 201:589-595, 1994.

Lubet et al, "A Pleiotropic Response to Phenobarbital-Type Enzyme Inducers in the F344/NCr RAT," *Chemical Pharmacology*, 43(5):1067-1078, 1992.

Lum et al., "Alteration of etoposide pharmacokinetics and pharmacodynamics by cyclosporine in a phase I trial to modulate multidrug resistance," *J. Clin. Oncol.*, 10:1635-1642, 1992.

Mackenzie et al., "Polymorphisms in UDP glucuronosyltransferase genes: functional consequences and clinical relevance," *Clin. Chem. Lab. Med.*, 38(9):889-892, 2000.

Mackenzie et al., "The UDP glycosyltransferase gene superfamily: recommended nomenclature update based on evolutionary divergence," *Pharmacogenetics*, 7:255-269, 1997.

Magdalou et al., "Peroxisome proliferators as inducers and substrates of UDP-glucuronosyltransferases," *Biol. Cell.*, 77(1):13-16, 1993.

Makhija et al., "Cytotoxicity of flavopiridol in ovarian cancer cells alone and in combination with CDDP," *Gynecoligic Oncology*, 68(1):83, Abstract #43, 1998.

Manning and Franklin, "Induction of rat UDP-glucuronosyltransferase and glutathione S-transferase activities by L-buthionine-S,R-sulfoximine without induction of cytochrome P-450," *Toxicology*, 65:149-159, 1990.

Mazzanti et al., "Bile acid inhibition of P-glycoprotein-mediated transport in multidrug-resistant cells and rat liver canalicular membrane vesicles," *Hepatology*, 20(1 Pt 1):170-176, 1994.

McKinney and Hosford, "ATP-stimulated tetraethylammonium transport by rabbit renal brush border membrane vesicles," *J. Biol. Chem.*, 268(10):6886-6895, 1993.

Mechetner and Roninson, "Efficient inhibition of P-glycoprotein-mediated multidrug resistance with a monoclonal antibody," *Proc. Natl. Acad. Sci. USA*, 89(13):5824-5828, 1992.

Meech and Mackenzie, "Determinants of udp glucuronosyltransferase membrane association and residency in the endoplasmic reticulum," *Arch Biochem Biophys.*, 356:77-85, 1998.

Michelson and Slate, "A Mathematical Model for the Inhibition of the Multidrug Resistance-Associated P-Glycoprotein Pump," *Bulletin of Mathematical Biology*, 56(2):207-223, 1994.

Miki and Kotake, "Advantages in combination chemotherapy using the camptothecin analogue CPT-11 and cisplatinum analogues for human testicular cancer xenografts," *Hinyokika Kiyo*, 39(12):1221-1225, 1993, English abstract.

Miller et al., "P-glycoprotein expression in malignant lymphoma and reversal of clinical drug resistance with chemotherapy plus high-dose verapamil," *J. Clin. Oncol.*, 9(1):17-24, 1991.

Miners and Mackenzie, "Drug glucuronidation in humans," *Pharmacol Ther.*, 51:347-369, 1991.

Miyamoto et al, "Multidrug resistance in yoshida rat ascites hepatoma cell lines," *Anticancer Res.*, 12(3):649-653, 1992.

Miyamoto et al., "Inhibition of multidrug resistance by a new staurosporine derivative, NA-382, in vitro and in vivo," *Cancer Res.*, 53(7):1555-1559, 1993.

Miyamoto et al., "Reversal of vinblastine resistance by a new staurosporine derivate, NA-382, in P388/ADR cells," *Cancer Lett.*, 64(2):177-183, 1992.

Monaghan et al., "Genetic variation in bilirubin UDP-glucuronosyltransferase gene promoter and Gilbert's syndrome," *Lancet*, 347:578-581, 1996.

Morris et al., "Interaction of forskolin with the P-glycoprotein multidrug transporter," *Biochemistry*, 30(34):8371-8379, 1991.

Muller et al., "ATP-dependent transport of amphiphilic cations across the hepatocyte canalicular membrane mediated by mdr1 P-glycoprotein," *FEBS Lett.*, 343(2):168-172, 1994.

Murthi et al., "Structure-activity relationship studies of flavopiridol analogues," *Bioorganic Med Chem Ltrs*, 10:1037-1041, 2000.

Narita et al., "Inhibition of Beta-Glucuronidase by Natural Glucuronides of *Kampo* Medicines Using Glucuronide of SN-38 (7-ethyl-10-hydroxycamptothecin) as a Substrate,"*Xenobiotica*, 23(1):5-10, 1993.

Nebert, "Pharmacogenetics and pharmacogenomics: why is this relevant to the clinical geneticist?" *Clin Gen*, 56:247-258, 1999.

Negoro et al., "Phase I Study of Weekly Intravenous Infusions of CPT-11, a New Derivative of Camptothecin, in the Treatment of Advanced Non-Small-Cell Lung Cancer," *Journal of the National Cancer Institute*, 83(16):1164-1168, 1991.

Niwa et al., "Effect of a dihydropridine analogue, 2-[benzyl(phenyl)amino]ethyl 1,4-dihydro-2,6-dimethyl-5-(5,5-dimethyl-2-oxo-1,3,2,-dioxaphosphorinan-2-yl)-1-(2-morpholino-ethyl)-4-(3-nitrophenyl)-3-(pyridinecarboxylate on reversing in vivo resistance of tumor cells to adrianmycin[1]," *Cancer Res.*, 52(13):3655-3660, 1992.

Ohe et al., "Phase I Study and Pharmacokinetics of CPT-11 With 5-Day Continuous Infusion," *Journal of the National Cancer Institute*, 84(12):972-974, 1992.

Ohi et al., "Intravesical instillation of adriamycin in the presence or absence of verapamil for the treatment of superficial bladder cancer: preliminary report of a collaborative study," *Cancer Chemother Pharmacol*, 30:S50-S54, 1992.

Okamura et al., "Digoxin-cyclosporin A interaction: Modulation of the multidrug transporter P-glycoprotein in the kidney," *J. Pharmacol. Exp. Therap.*, 266:1614-1619, 1993.

Owens and Ritter, "Gene structure at the human UGT1 locus creates diversity in isozyme structure, substrate specificity and regulation," *Progress in Nucleic Acid Research and Molecular Biology*, 51:305-338, 1995.

Owens and Ritter, "The novel bilirubin/phenol UDP-glucuronosyltransferase UGT1 gene locus: implications for multiple nonhemolytic familial hyperbilirubinemia phenotypes," *Pharamcogenetics*, 2:93-108, 1992.

Perdu and Germain, "Identification of novel polymorphisms in the pm5 and mrpl(abcc1) genes at locus 16p13.1 and exclusion of both genes as responsible for pseudoxanthoma elasticum," *Human Mutation*, 17:74-75, 2001.

Perez et al., "Mechanisms and Modulation of Resistance to Chemotherapy in Ovarian Cancer," *Cancer Supplement*, 71(4):1571-1580, Feb. 1993.

Pourtier-Manzanedo et al., "Expression of P-glycoprotein on normal lymphocytes: enhancement of the doxorubicin-sensitivity of concanavalin a—responding mouse spleen cells by P-glycoprotein blockers," *Oncol. Res.*, 4:473-480, 1992.

Prochaska and Fernandes, "Elevation of serum Phase II enzymes by anticarcinogenic enzyme inducers: markers for a chemoprotected state?," *Carcinogenesis*, 14(12):2441-2445, 1993.

Purba et al., "The metabolism of 17 α-ethinyloestradiol by human liver microsomes: formation of catechol and chemically reactive metabolites," *Br. J. Clin. Pharmacol.*, 23:447-453, 1987.

Radominska-Pandya et al., "Human UDP-glucuronosyltransferase 2B7," *Curr. Drug. Metab.*, 2:283-298, 2001.

Rajaonarison et. al., "In vitro glucuronidation of 3'-azido-3'-deoxythymidine by human liver," *Drug Metab. Disp.*, 19:809-815, 1993.

Ramirez et al., "In Vitro Characterization of Hepatic Flavopiridol Metabolism Using Human Liver Microsomes and Recombinant UGT Enzymes," *Pharm. Res.*, 19:588-594, 2002.

Ramírez et al.,. "In vitro glucuronidation of flavopridol (NSC649890) (flavo) by human liver microsomes," *Clin Pharmacol Ther*, 63:149, Abstract # PI-50, 1998.

Ratain et al., "Irinotecan Dosing: Does the CPT in CPT-11 Stand for "Can't Predict Toxicity"?" *J. Clin. Oncol.*, 20(1):7-8, 2002.

Ratain et al., "Paradoxal relationship between acetylator phenotype and amonafide toxicity," *Clin. Pharmacol. Ther.*, 50:573-579, 1991.

Ritter et al., "A novel complex locus UGT1 encodes human bilirubin, phenol and other UDP-glucuronosyltransferase isozymes with identical carboxyl termini," *J. Biol. Chem.*, 267:3257-3261, 1992.

Ritter et al., "Cloning of two humna liver bilirubin UDP-glucuronosyltransferase cDNAs with expression in COS-1 cells," *J. Biol. Chem.*, 226:1043-1047, 1991.

Robert, "Clinical pharmacokinetics of epirubicin," *Clin. Pharmacokinet*, 26:428-438, 1994.

Robey et al., "Overexpression of the atp-binding cassette half-transporter, abcg2 (mxr/bcrp/abcpl), in flavopiridol-resistnat human breast cancer cells," *Clinical Cancer Res.*, 7:145-152, 2001.

Rothenberg et al., "Phase I and Pharmacokinetic Trial of Weekly CPT-11," *Journal of Clinical Oncology*, 11(11):2194-2204, 1993.

Rowinsky et al., "Phase I and Pharmacological Study of the Novel Topoisomerase I Inhibitor 7-Ethyl-10-[4-(1-piperidino)-1-piperidino]carbonyloxycamptothecin (CPT-11) Administered as a Ninety-Minute Infusion Every 3 Weeks," *Cancer Research*, 54:427-436, 1994.

Rowinsky et al., "Taxol: Pharmacology, Metabolism and Clinical Implications," *Cancer Surv.*, 17:283-304, 1993.

Rund et al, "A mutation in the promoter of the multidrug resistance gene (mdr1) in human hematological malignancies may contribute to the patogenesis of resistant disease," *Adv. Exp Med Biol.*, 457:71-75, 1999.

Saeki et al., "Human P-Glycoprotein Transports Cyclosporin A and FK506," *The Journal of Biological Chemistry*, 268(9):6077-6080, 1993.

Sakata et al., "Preventive Effect of TJ-14, a Kampo (Chinese herb) Medicine, on Diarrhea Induced by *Irinotecan* Hydrochloride (CPT-11)," *Gan-To-Kagaku-Ryoho*, 21(8):1241-4, Jul. 1994; Abstract only.

Samuels et al., "Modulation of vinblastine resistance with cyclosporine: A phase I study," *Clin. Pharmacol. Ther.*, 54:421-429, 1993.

Sausville et al., "Cyclin-dependent kinases: initial approaches to exploit a novel therapeutic target," *Pharmacol Ther.*, 82:285-292, 1999.

Schinkel et al., "Disruption of the mouse mdr1 a P-glycoprotein gene leads to a deficiency in the blood-brain barrier and to increased sensitivity to drugs," *Cell*, 77(4):491-502, 1994.

Schrenk et al., "Induction of multidrug resistance gene expression during cholestasis in rats and nonhuman primates," *Hepatol.*, 17:854-860, 1993.

Schrump et al., "Flavopiridol mediates cell cycle arrest and apoptosis in esophageal cancer cells," *Clin Cancer Res.*, 4:2885-2890, 1998.

Senderowicz et al., "Phase I trial of continuous infusion flavopiridol, a novel cyclin-dependent kinase inhibitor, in patients with refractory neoplasms," *J Clin Oncol.*, 16:2986-2999, 1998.

Shapiro et al., "Flavopiridol induces cell cycle arrest and p53-independent apoptosis in non-small cell lung cancer cell lines," *Clin. Cancer Res.*, 5:2925-2938, 1999.

Sherr, "Cancer cell cycles," *Science*, 274:1672-1677, 1996.

Shirai et al., "Transport of cyclosporin A across the brain capillary endothelial cell monolayer by P-glycoprotein," *Biochim. Biophys. Acta*, 1222(3):400-404, 1994.

Sinicrope et al., "Modulation of P-glycoprotein-mediated transport by alterations in lipid fluidity of rat liver canalicular membrane vesicles," *J. Biol. Chem.*, 267:24995-25002, 1992.

Slichenmyer et al., "Camptothecin Analogues: Studies from The Johns Hopkins Oncology Center," *Cancer Chemother. Pharmacol.*, 34:S53-S57, 1994.

Slichenmyer et al., "The Current Status of Camptothecin Analogues as Antitumor Agents," *Journal of the National Cancer Institute*, 85(4):271-291, Feb. 1993.

Stadler et al., "Flavopiridol, a novel cyclin-dependent kinase inhibitor, in metastatic renal cancer: a university of chicago phase II consortium study," *J Clin Oncol.*, 18:371-375, 2000.

Stinson et al., "Determination of flavopiridol (L86 8275; NSC 649890) in human plasma by reversed-phase liquid chromatography with electrochemical detection," *Cancer Chemother. Pharmacol.*, 42(4):261-265, 1998.

Stocker, "Bilirubin is an antioxidant of possible physiological importance," *Science*, 235:1043-1046, 1987.

Strassburg et al., "Identification of cyclosporine A and tacrolimus glucuronidation in human liver and the gastrointestinal tract by a differentially expressed UDP-glucuronosyltransferase: UGT2B7," *J. Hepat.*, 34(6):865-872, 2001.

Suzuki, "Antitumor drugs and potentiators aiming circumvention of drug resistance," *Jpn J Cancer Chemother*, 17:335-341, 1990, English abstract.

Tamai and Safa, "Competitive interaction of cyclosporins with the vinca alkaloid-binding site of P-glycoprotein in multidrug resistant cells," *J. Biol. Chem.*, 265:16509-16513, 1990.

Taudou et al., "Inhibition of DNA Synthesis and DNA Fragmentation in Stimulated Splenocytes by the Concerted Action of Topoisomerase I and II Poisons," *Biochem. Pharmacol.*, 45(2):331-337, 1993.

Thalhammer et al., "Bile canalicular cationic dye secretion as a model for P-glycoprotein mediated transport," *Eur. J. Pharmacol.*, 270(2-3):213-220, 1994.

Thomas et al., "Phase I clincial and pharmacokineti trial of flavopiridol," *Proc Am Assoc Cancer Res*, 38:1496, Abstract #1496, 1997.

Toide et al., "Hepatocyte nuclear factor 1α is a causal factor responsible for interindividual differences in the expression of UDP-glucuronosyltransferase 2B7 mRNA in humna livers," *Drug Metabolism and Disposition*, 30(6):613-615, 2002.

Trump et al., "High-dose oral tamoxifen, a potential multidrug-resistance-reversal agent: phase 1 trial in combination with vinblastine," *J. Natl. Cancer Inst.*, 84(23):1811-1816, 1992.

Tsuruo et al., "Antitumor effect of CPT-11, a new derivative of camptothecin, against pleiotropic drug-resistant tumors in vitro and in vivo," *Cancer Chemother. Pharmacol.*, 21:71-74, 1988.

Tucker, "Clinical implications of genetic polymorphism in drug metabolism," *J. Pharm. Pharmacology*, 46:417-424, 1994.

Vezmar and Georges, "Reversal of mrp-mediated doxorubicin resistance with quinoline-based drugs," *Biochem Pharmacol.*, 59:1245-1252, 2000.

Vore, "Canalicular transport: Discovery of ATP-dependent mechanisms," *Toxicol. Appl. Pharmacol.*, 118:2-7, 1993.

Wade et al., "Variability in the pharmacokinetics of epirubicin: a population analysis," *Cancer Chemother. Pharmacol.*, 29:391-395, 1992.

Watanabe et al., "Kinetic Analysis of Hepatobiliary Transport of Vincristine in Perfused," *Journal of Hepatology*, 16:77-88, 1992.

Wilson et al., "A relationship between multidrug resistance and growth-state dependent cytotoxicity of the lysosomotropic detergent N-dodecylimidazole," *Biochem. Biophys. Res. Commun.*, 176(3):1377-1382, 1991.

Worland et al., "Alteration of the phosphorylation state of p34$^{cdc2}$ kinase by the flavone L86-8275 in breast carcinoma cells," *Biochem Pharmacol*, 46:1831-1840, 1993.

Zacherl et al., "Inhibition of P-Glycoprotein-Mediated Vinblastine Transport Across HCT-8 Intestinal Carcinoma Monolayers by Verapamil, Cyclosporine A and SDZ PSC 833 in Dependence on Extracellular pH," *Cancer Chemother. Pharmcol.*, 34:125-132, 1994.

Zhang et al., "Inhibitory Effects of Homoharringtonine and Hydroxycamptothecin in Combination with Other Agents on Cancer Cell Growth," *Asia Pac. J. Pharmacol.*, 7:191-195, 1992.

Ewesuedo and Ratain, "Topoisomerase I inhibitors," *Oncologist*, 2(6):359-364, 1997.

Guillamette et al., "Genetic polymorphisms in uridine diphospho-glucuronosyltransferase 1A1 and association with breast cancer among African Americans," *Cancer Res.*, 60:950-956, 2000.

Gupta et al., Modulation of glucoronidation of SN-38, the active metabolite of irinotecan, by valproic acid and phenobarbital, *Cancer Chemother. Pharmacol.*, 39(5):440-444, 1997.

Gupta et al, Pharmacokinetic modulation of irinotecan and metabolites by cyclosporin A., *Cancer Res.*, 56(6):1309-1314, 1996.

Innocenti et al., "Haplotypes of variants in the UDP-glucuronosyltransferase1A9 and 1A1 genes," *Pharmacogenetics and Genomics*, 15:295-301, 2005.

Innocenti et al., "Pharmacogenetics: a tool for individualizing antineoplastic therapy," *Clin. Pharmacokinet.*, 39(5):315-325, 2000.

Iyer et al., "Biliary transport of irinotecan and metabolites in normal and P-glycoprotein-deficient mice," *Cancer Chemother. Pharmacol.*, 49(4):336-341, 2002.

Iyer et al., "Genetic predisposition to the metabolism of irinotecan (CPT-11). Role of uridine diphosphate glucoronosyltransferase isoform 1A1 in the glucouronidation of its active metabolite (SN-38) in human liver microsomes," *J. Clin. Invest.*, 101(4):847-854, 1998.

Iyer et al., "Glucuronidation of TAS-103: A Novel Anticancer Agent," *Proc. Am. Soc. Clin. Oncol.*, 17:187a, No. 722, 1998.

Iyer et al., "Phenotype-genotype correlation of in vitro SN-38 (active metabolite of irinotecan_and bilirubin glucoronidation in human liver tissue with UGT1A1 promoter polymorphism," *Clin. Phamacol. Ther.*, 65(5):576-582, 1999.

Iyer et al., "UGT1A1*28 polymorphism as a determinant of irinotecan disposition and toxicity," *Pharmacogenetics J.*, 2(1):43-47, 2002.

Klein et al., "Population pharmacokinetic model for irinotecan and two of its metabolites, SN-38 and SN-38 glucoronide," *Clin. Pharmacol. Ther.*, 72(6):638-647, 2002.

Kroese et al., "Genetic tests and their evaluation: Can we answer the key questions?," Genetic in Medicine, 6:475-480, 2004.

Lucentini et al., "Gene Assocation Studies Typically Wrong," *The Scientist*, 20:1, Dec. 10, 2004.

Mani and Ratain, "Promising new agents in oncologic treatment," *Curr. Opin. Oncol.*, 8(6):525-534, 1996.

Mick et al., "Limited-sampling models for irinotecan pharmacokinetics-pharmacodynamics: prediction of bilary index and intestinal toxicity," *J. Clin. Oncol.*, 14(7):2012-2019, 1996.

Nakajima et al., "Involvement of multiple UDP-glucoronosyltransferase 1A isoforms in glucoronidation of 5-(4'-hydroxyphenyl-)-5-phenylhydantoin in human liver microsomes," Drug Metabolism and Disposition, 30(11):1250-1256, 2002.

Ratain, "Insights into the pharmacokinetics and pharmacodynamics of irinotecan," *Clin. Cancer Res.*, 6:3393-3394, 2000.

Sugatani et al., "Identification of a defect in the UGT1A1 gene promoter and its association with hyperbilirubinemia," *Biochem. Biophys. Res. Commun.*, 292(2):492-497, 2002.

Sugatani et al., "The phenobarbital response enhancer module in the human bilirubin UDP-glucuronosyltransferase UGT1A1 gene and regulation by the nuclear receptor CAR," *Hepatology*, 33(5):1232-1238, 2001.

Takahashi et al., "The Role of Glucuronidation in 7-Ethyl-10-hydroxycamptothecin Resistance in vitro," *Jpn. J. Cancer Res.*, 88:1211-1217, 1997.

Utsugi et al., "Antitumor Acitivity of a Novel Quinoline Derivative, TAS-103, with Inhibitory Effects on Topoisomerases I and II," *Jpn. J. Cancer Res.*, 88:992-1002, 1997.

Cote et al., "UGT1A1 polymorphism can predict hematologic toxicity in patients treated with irinotecan," *Clin. Cancer Res.*, 13(11):3269-3275, 2007.

Falandry et al., "Individual genotyping to optimize chemotherapy in metastatic colorectal cancer (MCRC): The COLOGEN trial," *J. Clin. Oncology*, 2007 ASCO Annual Meeting Proceedings Part I, 25(18S):2510, 2007.

Innocenti et al., "A genotype-directed phase I study of irinotecan in advanced cancer patients," *J. Clin. Oncology*, 2007 ASCO Annual Meeting Proceedings Part I, 25(18S):2502, 2007.

GenBank Accession No. NM_001074, Oct. 31, 2000.

Request for Ex Parte Reexamination of Patent No. 6,395,481, filed Jun. 22, 2005.

GenBank Accession No. AF297093, Feb. 7, 2002.

Order Granting Request for Ex Parte Reexamination of Patent No. 6,395,481, issued in U.S. Appl. No. 90/007,601, mailed Sep. 1, 2005.

Office Action in Ex Parte Reexamination of Patent No. 6,395,481, issued in U.S. Appl. No. 90/007,601, mailed Jun. 1, 2006.

Response to Office Action In re Ex Parte Reexamination of Patent No. 6,395,481, filed in U.S. Appl. No. 90/007,601, filed Aug. 1, 2006.

Supplemental Response to Office Action In re Ex Parte Reexamination of Patent No. 6,395,481, filed in U.S. Appl. No. 90/007,601, filed Aug. 17, 2006.

Notice of Intent to Issue Ex Parte Reexamination Certificate, issued in U.S. Appl. No. 90/007,601, mailed Sep. 1, 2006.

\* cited by examiner

```
-3565    TCTCTTCACCTCCTCCCTTATTCTCTTTTGACACTGGATTCTTTGCTTTGATAAATTGTGGGCAATACACTAGTAAAG
         NR4
-3486    GTCACTCAATTCCAAGGGGAAAATGATTAACCAAGAACATTCTAAGGGTTCATAAAGGGTATTAGGTGTAATGAGGAT
                                                          gtNR1
-3407    GTGTTACTCACCAGAACAAACTTCTGAGTTTATATAACCTCTAGTTACATAACCCTGAAACCCGGACTTGGCACTTGGT
-3328    AAGCACGCAATGAACAGTCATAGTAAGCTGGCCAAGGTAGAGTTCAGTTTGAACAAAGCAATTTGAGAACATCAAAGG
                                                 NR3
-3249    AAGTTTGGGGAACAGCAAGGGATCCAGAATGCTAGAGGGTAAGGGTAGAGGCAAGGTAGAGGCAAGAAGGCTAGAGA
-3170    GGAGGAATGAGCTTTGACAGGTGGGCTCATCCCAGAGTTTTGAGAGCAAGGCAGAGAGGACTCTGAATTTTCT

Variants
-3440C>A
-3401T>C
-3279G>T
-3177C>G
-3175A>G
-3156G>A
```

FIG. 4

METHODS FOR PREDICTING IRINOTECAN TOXICITY

This application is a national phase application under 35 U.S.C. §371 of International Application No. PCT/US2004/016920 filed 28 May 2004, which claims priority to U.S. Provisional Application No. 60/474,826 filed 30 May 2003. The entire text of each of the above-referenced disclosures is specifically incorporated herein by reference without disclaimer.

BACKGROUND OF THE INVENTION

1. Field of the Invention

The present invention relates generally to the fields of pharmacogenetics and cancer therapy. More particularly, it concerns methods and compositions for predicting or anticipating the level of toxicity of irinotecan and other compounds glucuronidated by a UGT enzyme in a patient. Such methods and compositions can be used to evaluate whether irinotecan-based therapy or therapy involving a UGT substrate may pose toxicity problems if given to a particular patient. Alterations in suggested therapy may ensue if toxicity may pose a problem.

2. Description of Related Art

Irinotecan is a topoisomerase I inhibitor that is approved worldwide for the treatment of metastatic colorectal cancer. Irinotecan has a well established role as single agent in 5-fluorouracil-refractory patients (Rougier et al., 1998; Cunningham et al., 1998), as well as in combination with 5-fluorouracil/leucovorin as a first-line therapy (Saltz et al., 2000; Rothenberg et al., 2001). Its role in the adjuvant setting is being explored.

Despite its efficacy in this disease and its broad spectrum of activity in other tumor types, irinotecan treatment is associated with significant toxicity. The main severe toxicities of irinotecan are delayed diarrhea and myelosuppression. In the early single agent trials, grade 3-4 diarrhea occurred in about one third of patients and was dose limiting (Negoro et al., 1991; Rothenberg et al., 1993). Its frequency varies from study to study and is also schedule dependent. The frequency of grade 3-4 diarrhea in the three-weekly regimen (19%) is significantly lower compared to the weekly schedule (36%, Fuchs et al., 2003). In addition to diarrhea, grade 3-4 neutropenia is also a common adverse event, with about 30-40% of the patients experiencing it in both weekly and three-weekly regimens (Fuchs et al., 2003; Vanhoefer et al., 2001). Fatal events during irinotecan treatment have been reported. A high mortality rate of 5.3 and 1.6% was reported in the weekly and three-weekly single agent irinotecan regimens, respectively (Fuchs et al., 2003).

While some information may be known about how to predict the patients who will eventually suffer intolerable toxicities (Ratain, 2002), additional information can be useful. Although this scenario seems discouraging, the risk of severe toxicity might be predicted by understanding the pharmacology of irinotecan and investigating the genetic variation of irinotecan metabolism. Irinotecan hydrolysis by carboxylesterase-2 is responsible for its activation to SN-38 (7-ethyl-10-hydroxycamptothecin), a topoisomerase I inhibitor of much higher potency than irinotecan (ref). The main inactivating pathway of irinotecan is the biotransformation of active SN-38 into inactive SN-38 glucuronide (SN-38G). Interpatient differences in systemic formation of SN-38G have been shown to have clear clinical consequences in patients treated with irinotecan. Patients with higher glucuronidation of SN-38 are more likely to be protected from the dose limiting toxicity of diarrhea in the weekly schedule (Gupta et al., 1994). SN-38 is glucuronidated by UDP-glucuronosyltransferase 1A1 (UGT1A1) (Iyer et al., 1997)

The UGT1A1 genetic variation has been extensively investigated in relation to hyperbilirubinemic syndromes, as UGT1A1 enzyme catalyzes the glucuronidation of bilirubin (ref). A variable number of repeats (5, 6, 7, and 8) have been found in the UGT1A1 TATA box. Gene transcriptional efficiency has been inversely correlated to the number of TA repeats (Beutler et al., 1998). Homozygosity for the (TA)$_7$ allele has been associated with the classical picture of Gilbert's syndrome, a common mild hyperbilirubinemia (Burchell et al.; Monaghan et al.). Gilbert's syndrome has also been associated with missense coding variants in the UGT1A1 gene, in particular in Asian populations where these variants are relatively common.

Because of the clinical importance of the glucuronidation pathway in irinotecan treatment, UGT1A1 is the candidate gene to be investigated in order to predict the events of severe toxicity after irinotecan treatment. Although retrospective analysis of UGT1A1 genetic variation in relation to severe toxicity after different irinotecan-based regimens has been conducted in Japanese patients (Ando et al., 2000), prospective evaluation in a large trial has not been performed.

SUMMARY OF THE INVENTION

The present invention is based on the observation that the nucleotide at position −3156 in the UGT1A1 upstream region is correlated with irinotecan toxicity. An A at that position positively correlates with irinotecan toxicity while a G at that position correlates with tolerance to irinotecan. Thus, the present invention concerns methods and compositions for evaluating, predicting, and determining whether a patient will experience toxicity from irinotecan. Toxicity from irinotecan evidences itself as side effects from the drug, which are well known to oncologists and their patients.

In some embodiments of the invention, there are methods of predicting whether a patient may suffer or be subject to toxicity from irinotecan if given that drug. Methods involve determining the nucleic acid sequence of base −3156 in the UGT1A1 promoter in one or both alleles of the patient. The presence of an A nucleotide indicates the person is at risk for irinotecan toxicity. An AA genotype is more closely correlated with grade 4 neutropenia than other genotypes at that position. Moreover, in some embodiments, this is unrelated to the genotype of the TA indel in the UGT1A1 promoter.

Consequently, if a person is identified as at risk for irinotecan toxicity, an alternative course of therapy or a lower dose of irinotecan than is normally given may be contemplated. In addition, methods also include determining the sequence of other polymorphisms or indels (insertion/deletions) in linkage disequilibrium (LED) with the −3156 variant. Therefore, in some embodiments of the invention, the TA indel is evaluated to determine the number of repeats. Also, any other variant in UGT1A1 or any other gene (the term "gene" includes non-coding regions that affect the expression or activity level of the encoded polypeptide) may be evaluated for variants in LED with the −3156 variant.

Compositions of the invention include nucleic acids that can be used to determine the sequence at position −3156 of UGT1A or other reagents in that regard. Arrays and other assays for screening multiple samples are also included as part of the invention.

Metabolism of SN-38, an active metabolite of irinotecan, via glucuronidation represents a mechanism to protect patients from the toxic effects of irinotecan, thus a reduction in SN-38 glucuronidation contributes to the probability that toxicity associated with irinotecan may be experienced in patients. While some genetic basis for reduced SN-38 glucuronidation have been identified, other basis have yet to be identified. Therefore, there remains a need for improved methods and compositions for evaluating polymorphisms in one or both UGT1A1 genes of a patient and correlating a genotype with adverse effects of various therapies.

The present invention is based on the fact that genetic variation is correlated with UGT1A1 expression and has several important clinical implications. The improved methods and compositions of the present invention may be used in determining if a treatment has a propensity to adversely affect a patient or what treatment may be appropriate or inappropriate for a particular patient. UGT1A1 basal transcription is affected by a polymorphic (TA) repeat (see FIG. 4, legend in Innocenti et al., 2002), in addition to a phenobarbital-responsive enhancer module (PBREM) that contains variants affecting inducible gene expression, as described herein. A "polymorphism" or "genetic polymorphism," as referred to herein, is the existence of two or more variant forms of a particular characteristic, e.g., a single nucleotide or a repeat a nucleotide or nucleotides. Generally, variations are due to the addition, deletion, or substitution of one or more nucleotides at a site or a variation in the number of tandem repeats of a DNA sequence. In various embodiments, other polymorphisms within or outside the UGT1 gene locus, see Genbank accession number AF297093 which is incorporated herein by reference, may be used as long as an association of a polymorphism with a particular phenotype and/or haplotype can be established. Exemplary methods for genotyping a UGT1A gene may be found at least in U.S. Pat. Nos. 6,479, 236, 6,472,157 and 6,395,481, each of which is incorporated herein by reference.

In various embodiments of the invention, significant linkage disequilibrium between a (TA) polymorphism and variants in the PBREM, or other variants within or outside the UGT1 gene locus, indicates that patients possessing such other variants may be at risk of irinotecan toxicity. "Significant" as used in respect to linkage disequilibrium, as determined by one of skill in the art, is contemplated to be a statistical p or α value that may be 0.25 or 0.1 and may be 0.1, 0.05. 0.001, 0.00001 or less. "Linkage disequilibrium" ("LD" as used herein, though also referred to as "LED" in the art) refers to a situation where a particular combination of alleles (i.e., a variant form of a given gene) or polymorphisms at two loci appears more frequently than would be expected by chance. The relationship between PBREM-(TA)$_n$ haplotypes and the glucuronidation rate of the UGT1A1 substrate SN-38 may be used to correlate the genotype (i.e., the genetic make up of an organism) to a phentoype (i.e., the physical traits displayed by an organism or cell). "Haplotype" is used herein to refer to a collective genotype of two or more closely linked loci. Each haplotype defines the sequence of alleles or polymorphisms along one of the homologous chromosomes. In some embodiments, the polymorphisms may be 0.001, 0.01, 0.1, 0.2 cM or more within one another.

Various embodiments of the invention include methods for evaluating the risk of toxicity from irinotecan, or other UGT1A1 substrates, in a patient. A polymorphism may be a single nucleotide polymorphism (SNP) and may be in linkage disequilibrium with a (TA)$_n$ repeat. In certain embodiments, the methods include detecting one or more polymorphisms in one or both copies of the UGT1A1 gene and/or one or both copies of any other gene located in the UGT1 gene locus of a patient. In particular embodiments a promoter polymorphism is detected. It is specifically contemplated that methods and compositions of the invention may be implemented to determine whether UGT1A1 polymorphisms are present or absent in one or both alleles.

In certain embodiments, a polymorphism may be a polymorphism that affects the transcription of UGT1A1, such as in the promoter region or 5' flanking region that affects transcription (which includes the promoter region), and in particular a polymorphism at nucleotide position −3440, −3401, −3279, −3177, −3175, or −3156 from the UGT1A1 gene transcriptional start site, which is designated +1 with no nucleotide designated as 0. The number of TA repeats can be 5, 6, 7, 8 or more TA repeats. In particular embodiments, the polymorphism is the following: −3440C>A, −3401T>C, −3279G>T, −3177C>G, −3175A>G, −3156G>A, or any combination thereof. The notation −3440C>A, for example indicates that cytosine nucleotide (C) at the −3440 position is replaced by an Adenosine (A).

Methods of the invention may include obtaining a nucleic acid sample from a patient and detecting one or more polymorphisms in the UGT1A1 gene using various methods. In certain embodiments, polymorphism detection may include amplifying a nucleic acid containing all or part of a particular region of the UGT1A1 gene to obtain amplification products; and/or analyzing the amplification products for the presence or absence of one or more polymorphisms. Other methods of polymorphism detection known in the art are also contemplated.

In certain embodiments, a promoter polymorphism of a UGT1A1 gene may be detected by performing one of a variety of known assays. These may include, but are not limited to hybridization assays, sequencing or microsequencing assays, allele-specific amplification assays or any other methods known for detecting nucleic acid polymorphisms, which may or may not include amplification of a nucleic acid. It is understood that "detecting" a polymorphism includes identifying the nucleotide sequence at that site and/or determining whether the polymorphism is present or absent.

A correlation between one or more polymorphisms and the glucoronidation rate of irinotecan or other substrates of UGT1A1, including but not limited to bilirubin, estriol, beta-estradiol, 2-hydroxyestriol, 2-hydroxyestrone, 2-hydroxyestradiol, thyroxine (T4), rT3, octyl gallate, propyl gallate, anthraflavic acid, quercitin, fisetin, naringenin, 1-naphtol, and ethynylestradiol, may be used to determine various aspects of a treatment regime, including irinotecan and/or other drugs or compounds metabolized directly or indirectly by UGT1A1. In some embodiments the methods also include analyzing the glucuronidation rate associated with the various polymorphisms and polymorphism combinations, for exemplary methods and compositions related to analysis of glucuronidation rates see U.S. Pat. No. 6,319,678, which is incorporated herein by reference. The methods may also include determining the biliary transport capacity of the patient. In particular embodiments the evaluation of the promoter polymorphism may be used to optimize the dose of irinotecan or other compounds for treatment of a patient or to reduce their toxicity.

The methods of the invention may further include treating a patient by administering to the patient irinotecan in combination with other pharmaceutical agents at appropriate dosages, such that the toxicity of irinotecan or other substrates of UGT1A1 are reduced. In particular embodiments, a second agent that reduces excretion of an active irinotecan species through the bile may administered in conjunction with irinotecan based upon determinations made using methods and compositions of the invention, for related methods and compositions see U.S. Pat. Nos. 6,407,117, 6,287,834 and 5,786,344, each of which is incorporated herein by reference.

The present invention is also based on the observation that the nucleotide at position −3156 in the UGT1A1 upstream region is correlated with irinotecan toxicity. An A at that position positively correlates with irinotecan toxicity while a G at that position correlates with tolerance to irinotecan. Thus, the present invention concerns methods and compositions for evaluating, predicting, and determining whether a patient will experience toxicity from irinotecan. Toxicity from irinotecan evidences itself as side effects from the drug, which are well known to oncologists and their patients.

In some embodiments of the invention, there are methods of predicting whether a patient may suffer or be subject to toxicity from irinotecan if given it involving determining the nucleic acid sequence of base −3156 in the UGT1A1 5' flanking region in one or both alleles of the patient. The presence of an A nucleotide indicates the person is at risk for irinotecan toxicity. An AA genotype is more closely correlated with grade 4 neutropenia than other genotypes at that position. Moreover, in some embodiments, this is unrelated to the genotype of the TA indel in the UGT1A1 promoter. It is contemplated that these methods concerning the indel at position −3156 in the UGT1A1 5' flanking region can be implemented with methods involving determining one or more other polymorphisms in the UGT1A1 5' flanking region of the same patient.

Consequently, if a person is identified as at risk for irinotecan toxicity based on any of the embodiments discussed herein, an alternative course of therapy or a lower dose of irinotecan than is normally given may be contemplated. In addition, methods also include determining the sequence of other polymorphisms or indels (insertion/deletions) in linkage disequilibrium (LD) with the −3156 variant. Therefore, in some embodiments of the invention, the TA indel is evaluated to determine the number of repeats. Also, any other variant in UGT1A1 or any other gene (the term "gene" includes non-coding regions that affect the expression or activity level of the encoded polypeptide) may be evaluated for variants in LD with the −3156 variant.

Various embodiments may include a kit for evaluating the risk of irinotecan toxicity in a patient. The kit may include a variety of containers, reagents and the like. In certain embodiments, the kit may include an oligonucleotide primer to amplify a promoter region of a UGT1A1 gene or genes, haplotype tag SNPs or allele specific amplification primers of the UGT1A1 gene or any other primer within the UGT1 gene locus. The haplotype tag SNPs or allele specific primers may be used to amplify a polymorphism at one or more nucleotide positions of the UGT1A1 gene or other UGT1 gene locus. In particular embodiments, the nucleotide position may be at −3440, −3401, −3279, −3177, −3175, or −3156, or a combination thereof, from the UGT1A1 gene transcriptional start site. The kit may include the haplotype tag SNPs or allele specific amplification primers in multi-well assay plate. The kit may also include haplotype tag SNPs or allele specific hybridization probes for a variety of promoter polymorphisms. The haplotype tag SNPs or allele specific hybridization probes may detect polymorphisms at nucleotide position −3440, −3401, −3279, −3177, −3175, or −3156 from the UGT1A1 gene transcriptional start site. The kit may include haplotype tag SNPs or allele specific hybridization probes comprised in an oligonucleotide array or microarray.

Compositions of the invention include nucleic acids that can be used to determine the sequence at position −3156 of UGT1A or other reagents in that regard. Arrays and other assays for screening multiple samples are also included as part of the invention. Such compositions may be incorporated into kits or as part of a kit, along with any other composition discussed herein.

It is specifically contemplated that any embodiment of any method or apparatus of the invention may be used with respect to any other method or apparatus of the invention.

The use of the term "or" in the claims is used to mean "and/or" unless explicitly indicated to refer to alternatives only or the alternative are mutually exclusive, although the disclosure supports a definition that refers to only alternatives and "and/or."

Throughout this application, the term "about" is used to indicate that a value includes the standard deviation of error for the device or method being employed to determine the value.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 4. Phenobarbital-responsive enhancer module (PBREM) and description of mutations (SEQ ID NO: 14).

DESCRIPTION OF ILLUSTRATIVE EMBODIMENTS

Figure 1:
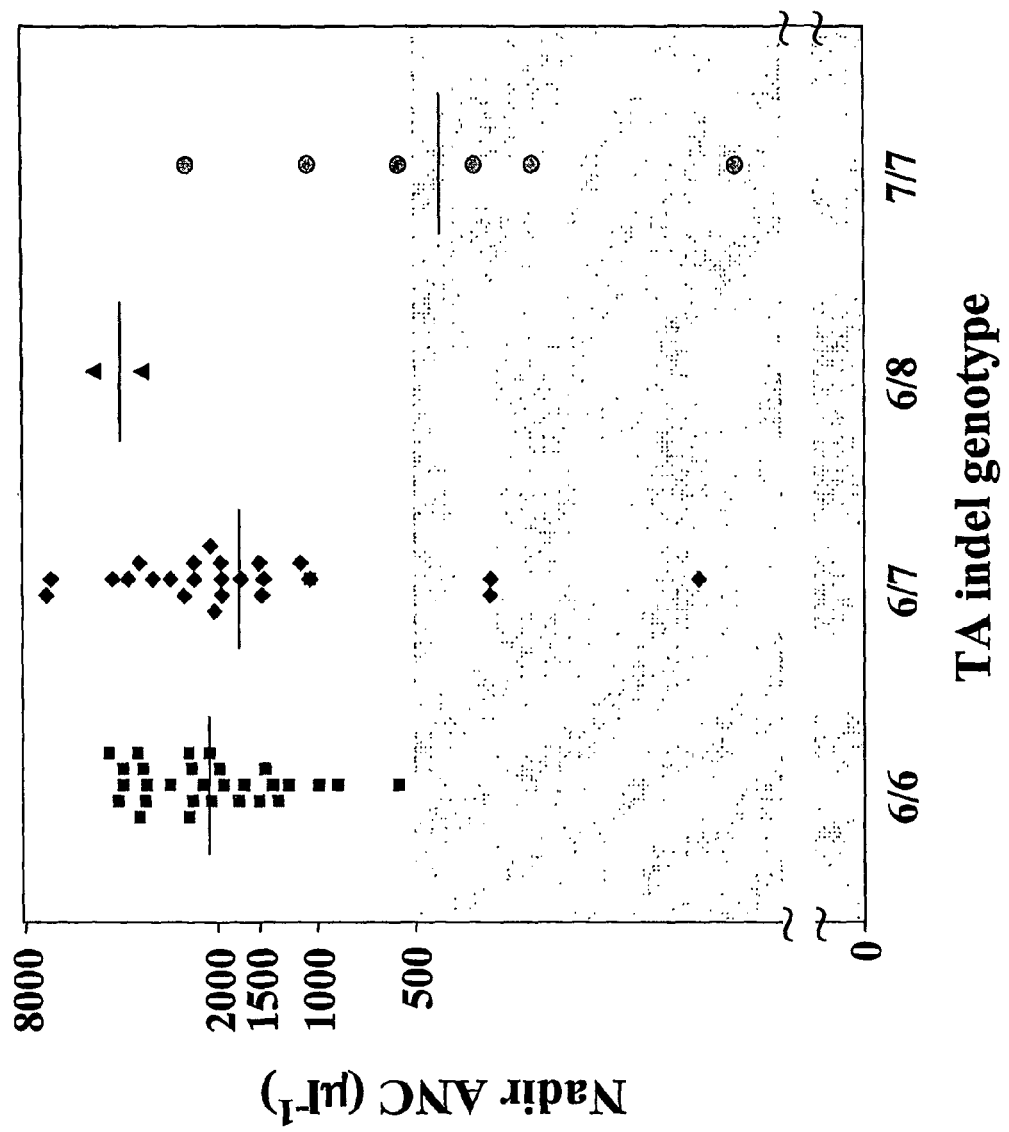
FIG. 1. Correlation between ANC and TA indel genotype. Bars represent the means. Nonparametric trend analysis (7/7<6/7<6/6, z=−2.72, p=0.01).
Figure 2:
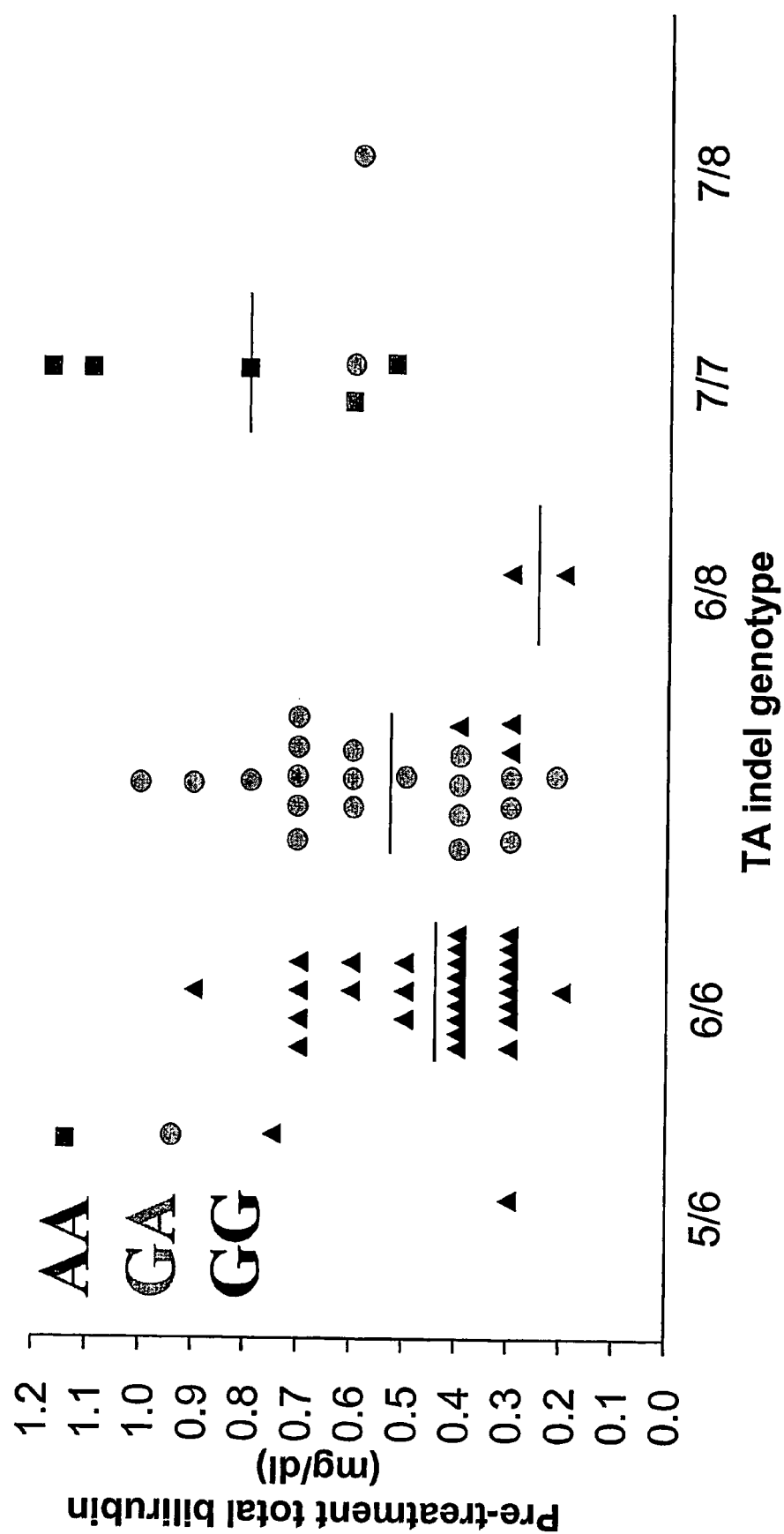
FIG. 2. Pre-treatment total bilirubin levels and distribution of the −3156 genotypes within each TA indel genotype. The −3156 AA genotypes are reported in squares, the GA genotypes in circles and the GG genotypes in triangles. Bars represent the mean values. A significant trend was reported (7/7>6/7>6/6, z=2.88, p<0.01, nonparametric trend analysis).

The following patent applications and patents are hereby incorporated by reference in their entirety: U.S. Pat. Nos. 6,395,481, 6,472,157, Application Publication Nos. 2003-0152968, and 2003-0099960.

The present invention provides improved methods and compositions for identifying the effects of various polymorphisms, promoter polymorphisms or any combination thereof on the expression of UGT1A1 or the glucuronidation rate of UGT1A1 for the evaluation of the potential or risk for irinotecan toxicity in an individual or patient. The development of these improved methods and compositions allows for the use of such an evaluation to optimize treatment of a patient and to lower the risk of toxicity. In certain aspects of the invention various combinations of promoter polymorphisms may be used in this evaluation, in particular, polymorphisms in the PBREM region and polymorphisms in the TA repeats may be used.

Genetic variation in UGT1A1 expression has several important clinical implications. UGT1A1 basal transcription is affected by a polymorphic (TA) repeat. Another important regulatory element is the phenobarbital-responsive enhancer module (PBREM) which may contain variants affecting inducible gene expression. The examples provided herein study the extent of linkage disequilibrium between the (TA) polymorphism and variants in the PBREM and UGT1A1 promoter. The relationship between PBREM-(TA)$_n$ haplotypes and the glucuronidation rate of the UGT1A1 substrate SN-38 is also addressed herein. Studies described in the Examples illustrate that SN-38G formation rates were correlated with (TA) genotypes and promoter variants. In various aspects particular (TA) variants are in linkage disequilibrium with various other polymorphisms.

Certain aspects of the invention are based on, but not limited to, the observation and characterization of novel polymorphisms in the PBREM region of the UGT1A1 gene. Due to the clinical implications of genetically modified regulation of UGT1A1 activity, the PBREM region was sequenced and polymorphisms in the TATA box of the UGT1A1 promoter genotyped, as described in the Examples section below.

I. Hepatic Glucuronidation by UGT Enzymes

Hepatic glucuronidation results from the activities of a multigene family of UGT enzymes, the members of which exhibit specificity for a variety of endogenous substrates and xenobiotics. The UGT enzymes are broadly classified into two distinct gene families. The UGT1 locus codes for multiple isoforms of UGT, all of which share a C-terminus encoded by a unique set of exons 2-5, but which have a variable N-terminus encoded by different first exons, each with its own independent promoter (Bosma et al., 1992; Ritter et al., 1992). The variable first exons confer the substrate specificity of the enzyme. Isoforms of the UGT2 family are unique gene products of which at least eight isozymes have been identified (Clarke et al. Handbook of Experimental Pharmacology 1994). The UGT1A1 isoform is the major bilirubin glucuronidation enzyme. Genetic defects in the UGT1A1 gene can result in decreased glucuronidation activity which leads to abnormally high levels of unconjugated serum bilirubin that may enter the brain and cause encephalopathy and kernicterus (Owens & Ritter, 1995). This condition is commonly known as Gilbert's syndrome. The molecular defect in Gilbert's Syndrome is a change in the TATA box within the UGT1A1 promoter (Bosma et al., 1995 and Monaghan et al., 1996). This promoter usually contains a (TA)$_6$ TAA element, but another allele, termed UGT1A1*28 or allele 7, is also present in human populations at high frequencies, and contains the sequence (TA)$_7$ TAA. This polymorphism in the promoter of the UGT1A1 gene results in reduced expression of the gene and accounts for most cases of Gilbert's Syndrome (Bosma et al., 1995). Overall, gene expression levels for the UGT1A1 promoter alleles are inversely related to the length of the TA repeat in the TATA box.

The variation observed in this promoter may also account for the inter-individual and inter-ethnic variation in drug metabolism and response to xenobiotic exposure.

UGTs have been shown to contribute to the detoxification and elimination of both exogenous and endogenous compounds. For example, one typical role of the UGT1A1 isoform is the glucuronidation of SN-38 (7-ethyl-10-hydroxycamptothecin) to the corresponding glucuronide (10-O-glucuronyl-SN-38, SN-38G) as well as the glucuronidation of TAS-103 (6-[[2-(dimethylamino)ethyl]amino]-3-hydroxy-7H-indeno[2,1-c]quinoline-7-one dihydrochloride) to its corresponding glucuronide (TAS-103G). SN-38 is the active form of irinotecan (CPT-11, 7-ethyl-10-[4-(1-piperidino)-1-piperidino]carbonyloxycamptothecin), which is a camptothecin derivative used in the treatment of metastatic colorectal cancer and other malignancies. The metabolism of SN-38 and TAS-103 (also known as flavopiridol) are merely illustrative of the present invention the metabolism of other UGT1A1 substrates is also contemplated, such as estradiol, bilirubin, simple phenols, flavones, C18 steroids, complex phenols and coumarins.

Irinotecan is biotransformed by tissue and serum carboxylesterases to an active metabolite, SN-38, which has a 100-1,000-fold higher antitumor activity than irinotecan. SN-38 is glucuronidated by hepatic uridine diphosphate glucuronosyltransferases (UGTs) to form SN-38 glucuronide (10O-glucuronyl-SN-38, SN-38G), which is inactive and excreted into the bile and urine although, SN-38G might be deconjugated to form SN-38 by intestinal β-glucuronidase enzyme (Kaneda et al., 1990).

The major dose-limiting toxicities of irinotecan include diarrhea and, to a lesser extent, myelosuppression. irinotecan-induced diarrhea can be serious and often does not respond adequately to conventional antidiarrheal agents (Takasuna et al., 1995). This diarrhea may be due to direct enteric injury caused by the active metabolite, SN-38, which has been shown to accumulate in the intestine after intra peritoneal administration of irinotecan in athymic mice (Araki et al., 1993). The results of a recently completed phase I clinical trial, demonstrated that there was an inverse relationship between SN-38 glucuronidation rates and severity of diarrheal incidences in patients treated with increasing doses of Irinotecan (Gupta et al., 1994). These findings indicate that glucuronidation of SN-38 protects against Irinotecan-induced gastrointestinal toxicity. A complete discussion of the correlation between diarrhea and SN-38 glucuronidation, as well as a description of biochemical methods for determining glucurondation levels can be found in U.S. Pat. No. 5,786,344 and WO96/01127 which are both incorporated herein by reference in their entirety. Likewise, the results of studies using TAS-103 demonstrate that glucuronidation of TAS-103 may protect against TAS-103 induced toxicity. Therefore, the conversion of these two toxic compounds by hepatic UGTs demonstrates the importance of monitoring glucuronidation activity as an indicator of susceptibility to toxicity caused by exposure to compounds that are metabolized by UGTs. Furthermore, differential rates of SN-38 glucuronidation among subjects may explain the considerable inter-individual variation in the pharmacokinetic parameter estimates and toxicities observed after treatment with anti-cancer drugs or exposure to xenobiotics (Gupta et al., 1994; Gupta et al., 1997).

When two species, Gunn rats (Gunn, 1938) and CN-1 patients, that are deficient in UGT1Aisoforms were screened for TAS-103 and SN-38 glucuronidation activity, there was approximately an 80% lower glucuronidation rate of TAS-103 in vitro and no in vitro glucuronidation of SN-38 compared to healthy liver donors. These results demonstrate the role of the UGT1 family in catalyzing SN-38 and TAS-103 conjugation. Furthermore, these results demonstrate that the UGT2 family does not play a role in the glucuronidation of SN-38. On the other hand, while isoforms of the UGT1 family are the predominate isoforms involved in TAS-103 glucuronidation, the isoform of the UGT2 family may also participate in TAS-103 glucuronidation. Failure to glucuronidate SN-38 and TAS-103 in these instances may result specifically from the genetic defect in UGT1 gene family.

Other experiments confirm the association between the UGT1A1 isoform and SN-38 and TAS-103 glucuronidation. These studies show that substantial genetic variability exists in the UGT1A1 isoform family and particularly in the UGT1A1 promoter. This genetic variability has been shown to correlate with gene expression. For example, the presence of the 5 allele in the UGT1A1 promoter leads to increased gene expression while the presence of the 8 allele leads to reduced gene expression. Differences in gene expression levels may give rise to individuals with varying abilities to glucuronidate compounds metabolized by UGTs. This prediction was confirmed through a correlation analysis of UGT1A1 promoter genotype and rate of in vitro SN-38 and TAS-103 glucuronidation.

It follows therefore that individuals with the 8 allele may also have differing susceptibility to xenobiotics when compared to other genotypes when those compounds are metabolized by UGT1A1s. On the other hand, the presence of the 5 allele that correlates with increased gene expression and higher glucuronidation activity may result in the administration of less than optimum drug dosages. For example, when a drug metabolized by UGT1A1s is administered to an individual with this polymorphism, the increased glucuronidation activity may cause more of the drug to be converted into the inactive metabolite in a shorter period, thereby reducing the drug's effectiveness. Conversely, in the rare case of drugs and xenobiotics that require glucuronidation for activation, decreased glucuronidation activity may cause less of the activated form of the drug or xenobiotic to be available.

The fact that repeated sequences are intrinsically unstable and tend to lengthen and shorten as a result of unequal crossing-over during meiosis may explain the presence of other alleles, in addition to $(TA)_6$ and $(TA)_7$, in the population. Two additional alleles have been identified in human populations: allele 5, containing the sequence $(TA)_5$ TAA and allele 8, containing the sequence $(TA)_8$ TAA, see U.S. Pat. No. 6,395,481, which is incorporated in its entirety by reference. Interestingly, alleles 5 and 8 were found predominantly in population samples from Sub-Saharan Africa, where they occur at lower frequencies than the common alleles 6 and 7 although it is possible that these two alleles are present across a variety of ethnic groups. The frequency of alleles 6 and 7 also appears to differ significantly across ethnic groups, with Asian and Amerindian populations showing the highest frequencies of allele 6. Conversely, alleles 6 and 7 occur at intermediate and similar frequencies among Caucasians and Sub-Saharan Africans.

Several hypotheses may be proposed regarding the selective pressures that might be responsible for the observed pattern of inter-population variation at the UGT1A1 promoter. It was previously proposed that the maintenance of intermediate levels of bilirubin is adaptive (Beutler et al., 1998), and that the alleles at this promoter would be maintained in the population by balancing selection. This hypothesis is based on the observation that bilirubin is a potent antioxidant likely to have physiological significance (Stocker et al., 1987). However, it is also known that glucuronidation is an important detoxification step for many endogenous as well as exogenous compounds (Clarke & Burchell, 1994). In addition to TAS-103 and SN-38, UGT1A1 is likely to act on other substrates present in the environment, e.g., dietary components, environmental pollutants and carcinogens, which require detoxification as well as playing a role in the metabolism of bilirubin and other endogenous compounds. Within this framework, maintaining high levels of UGT1A1 gene expression would ensure rapid elimination of toxic or endogenous compounds and be advantageous.

As described herein, the correlation between in vitro glucuronidation rate and UGT1A1 promoter polymorphism found for alleles 6 and 7 has been shown to extend to alleles 5 and 8. Because these alleles appear to be more frequent in subsets of human populations (for example, those of African origin), an even higher inter-individual variability in SN-38 and TAS-103 metabolism might be expected within these populations. Because the inverse relationship between TA repeat size and rate of SN-38 glucuronidation extends to alleles 5 and 8, a screening assay that identifies these alleles can facilitate individualization of drug therapy, identify individuals susceptible to xenobiotic exposure, and can be used to improve drug dosage calculations.

A. Previous Experiments Involving UGT1A1

Experiments involving UGT1A1 are described in U.S. patent application Ser. No. 10/751,606 filed on Jan. 5, 2004, which is hereby incorporated by reference herein. These experiments are described below.

1. Genotyping of $(TA)_N$ Polymorphism

The $(TA)_6$ allele was the most common allele with a frequency of 0.58 while the $(TA)_7$ allele had a frequency of 0.36 (table below). $(TA)_5$ and $(TA)_8$ alleles were also found, although at lower frequencies (0.02 and 0.05, respectively). In the population sample (n=107), the most common genotype was 6/7 (0.41), followed by the 6/6 genotype (0.34). Rare genotypes (<0.02) included 5/6, 5/7 and 5/8 genotypes. The $(TA)_6$ and $(TA)_7$ allele frequencies were not significantly different between Caucasians and African-Americans (chi-square test, P=0.7). Similarly, 6/6, 6/7, and 7/7 genotype frequencies were not different between the two ethnic groups (chi-square test, P=0.8). One Asian individual had a 6/6 genotype, while two individuals with other ethnicities had 6/7 and 7/7 genotypes.

| | $(TA)_n$ polymorphism: genotype frequencies | | | | | | | |
|---|---|---|---|---|---|---|---|---|
| | $(TA)_n$ | | | | | | | |
| | 5/6 | 5/7 | 5/8 | 6/6 | 6/7 | 6/8 | 7/7 | 7/8 |
| Population Sample (n = 107) | 0.01 | 0.02 | 0.01 | 0.34 | 0.41 | 0.06 | 0.13 | .03 |
| Caucasians (n = 56) | 0.02 | 0 | 0 | 0.38 | 0.46 | 0 | 0.13 | 0.02 |
| African-Americans (n = 39) | 0 | 0.05 | 0.03 | 0.26 | 0.33 | 0.15 | 0.13 | 0.05 |

2. Sequencing of PBREM

In 103 samples, six polymorphisms were found, and two of them (−3279G>T and −3156G>A) are common, with frequencies of 0.39 and 0.30, respectively (FIG. 4, Table below). All six polymorphisms are in Hardy-Weinberg equilibrium (P>0.5). Based upon comparisons to the baboon sequence (accession number AC091778, which is incorporated herein by reference), it is likely that −3279G and −3156G are the ancestral states. The most common −3279G>T polymorphism is located in the spacer sequence of the NR3 domain of PBREM (FIG. 4). No variants were found in the gtNR1 domain, the binding site for constitutive active receptor (CAR). −3279G was significantly more common among African-Americans compared to Caucasians (chi squared=13.82, P=0.001) while the frequency of −3156A did not significantly differ between the two ethnic groups (chi-square test, P=0.9).

Multisite haplotype inference resulted in 10 haplotypes spanning the PBREM variants and the $(TA)_n$ polymorphism (table below). Haplotypes I-V include the $(TA)_6$ allele, and haplotype I differs from haplotype II at position −3279 in the NR3 domain of PBREM. Haplotypes VI, VII and VIII include the $(TA)_7$ repeat and haplotypes VI and VII differ from each other at position −3156. There is a suggestion that the haplo- Sequencing of PBREM: genotype frequencies

| | Position | | | | | | | | | | | | | |
|---|---|---|---|---|---|---|---|---|---|---|---|---|---|---|
| | −3440 | | −3401 | | −3279 | | | −3177 | | −3175 | | −3156 | | |
| Genotype | CC | CA | TT | TC | GG | GT | TT | CC | CG | AA | AG | GG | GA | AA |
| Population Sample (n = 103) | 0.96 | 0.04 | 0.99 | 0.01 | 0.38 | 0.46 | 0.16 | 0.99 | 0.01 | 0.99 | 0.01 | 0.49 | 0.43 | 0.08 |
| Caucasian (n = 55) | 0.96 | 0.04 | 1 | 0 | 0.18 | 0.58 | 0.24 | 1 | 0 | 1 | 0 | 0.47 | 0.44 | 0.09 |
| African-Americans (n = 37) | 0.95 | 0.05 | 0.97 | 0.03 | 0.73 | 0.24 | 0.03 | 0.97 | 0.03 | 0.97 | 0.03 | 0.51 | 0.41 | 0.06 |

3. Linkage Disequilibrium and Haplotype Structure of the UGT1A1 Promoter

A likelihood ratio test detected significant pairwise linkage disequilibrium between sites −3279, −3156 and the $(TA)_7$ polymorphism in our population sample (n=103, P<0.0001). When only the common $(TA)_6$ and $(TA)_7$ alleles were used for the linkage disequilibrium analysis, the same results were obtained (P<0.0001). When pairwise linkage disequilibrium was separately assessed in Caucasians and African-Americans, highly significant linkage disequilibrium was similarly detected in Caucasians (P<0.0001). In African-Americans, pairwise linkage disequilibrium was also detected between all sites, however, the level of significance varied greatly between the pairwise comparisons. Only linkage disequilibrium between $(TA)_n$ and −3156 had significance levels similar to those seen for Caucasians (P<0.0005) while linkage disequilibrium had only low levels of significance between $(TA)_n$ and −3279 (P=0.02) and between −3279 and −3156 (P=0.04).

type structure of the $(TA)_6$ allele is different in the African-American subsample. Compared to Caucasians, haplotype I is less common in African-Americans (chi squared=27.06, P<0.0001), while haplotype II is more common (chi squared=14.84, P=0.0001). Differences in haplotype VI and VII frequencies were not statistically significant between the two groups (chi-square test, P=0.44 and 0.48, respectively).

Among the samples examined, 21 different combinations of these haplotypes were found. In Caucasians, the most frequent haplotype pairs are I/VI (0.35), I/I (0.24) and I/II (0.11), while in African-Americans, they are I/II (0.11), II/VI (0.11), II/VIII (0.08), I/VI (0.08), II/VII (0.08) and VI/VI (0.08). The effective numbers of haplotypes, which reflect how many relatively high frequency haplotypes are observed, were 5.2 and 2.6 in African-Americans and Caucasians, respectively (table below). Finally, diversity (±SD) of $(TA)_6$ haplotypes was 0.555±0.070 and 0.262±0.065 in African-Americans and Caucasians, respectively (P<0.05).

Haplotype structure of promoter mutations and haplotype frequencies. The effective number of haplotypes is also reported.

| Haplotype | −3440 | −3401 | −3279 | −3177 | −3175 | −3156 | $(TA)_n$ | Population Sample (n = 103) | Caucasians (n = 55) | African-Americans (n = 37) |
|---|---|---|---|---|---|---|---|---|---|---|
| I | C | T | T | C | A | G | $(TA)_6$ | 0.39 | 0.53 | 0.15 |
| II | C | T | G | C | A | G | $(TA)_6$ | 0.15 | 0.07 | 0.28 |
| III | A | T | G | C | A | G | $(TA)_6$ | 0.02 | 0.02 | 0.03 |
| IV | C | C | G | C | A | G | $(TA)_6$ | 0.01 | 0 | 0.01 |
| V | C | T | G | C | A | A | $(TA)_6$ | 0.01 | 0 | 0.01 |
| VI | C | T | G | C | A | A | $(TA)_7$ | 0.29 | 0.31 | 0.28 |
| VII | C | T | G | C | A | G | $(TA)_7$ | 0.07 | 0.05 | 0.08 |
| VIII | C | T | G | G | G | A | $(TA)_7$ | 0.01 | 0 | 0.01 |
| IX | C | T | G | C | A | G | $(TA)_8$ | 0.05 | 0.01 | 0.12 |
| X | C | T | G | C | A | G | $(TA)_5$ | 0.02 | 0.01 | 0.04 |
| | | | | | | | | $3.7^a$ | $2.6^a$ | $5.2^a$ |

4. UGT1A1 Phenotyping and Association with (TA)n Polymorphism and Haplotypes UGT1A1 activity was measured as SN-38 glucuronidation rates in 83 human liver microsomes. A 46% coefficient of variation (1.90 f 0.87 SN-38G/IS, mean f SD) and a 10-fold range in SN-38 glucuronidation were observed.

Because of the small number of subjects in the 5/7, 5/6, 6/8 and 7/8 genotypes, only 6/6, 6/7 and 7/7 were used in the ANOVA analysis. The phenotype was significantly different across these three genotypes ($P=0.008$) (FIG. 5A). The degree of variation of the SN-38 glucuronidation rate across the genotypes was similar in different ethnic groups ($P>0.1$). A significantly decreasing trend was shown across the 6/6, 6/7 and 7/7 genotypes in Caucasians ($P<0.001$, JT test, FIG. 5B) and across the 6/6, 6/7, 6/8 and 7/7 genotypes in African-Americans ($P=0.033$, JT test) (FIG. 5C). When samples with Asian ($n=1$), other ($n=2$) and unknown ($n=10$) ethnic background were pooled together, no significant trend could be found across $(TA)_n$ genotypes ($P>0.1$, JT test) (FIG. 5D). In the Caucasian sample, pairwise comparisons of the phenotype between two genotype groups showed significant differences between the 6/7 and 7/7 ($P=0.007$, one-sided exact Wilcoxon test) and 6/6 and 7/7 groups ($P=0.0002$). No pairwise comparison was significant within African-Americans, probably due to small number of samples of each genotype.

When $(TA)_n$ genotypes were regarded as the sum of TA repeat number in both chromosomes (i.e. $\leq 12$ (5/6, 6/6, 5/7), 13 (6/7) and $\geq 14$ (7/7, 6/8, 7/8) genotypes), a significant trend of reduced UGT1A1 activity ($P<0.01$) was measured across the three groups (the lowest being the $\geq 14$ genotype group) in the whole sample population, in Caucasians, in African-Americans but not in samples with Asian/other/unknown ethnicity ($P=0.66$). Pairwise comparisons (one-sided exact Wilcoxon test) showed significantly reduced UGT1A1 activity ($P<0.01$) in $\geq 14$ compared to 13 and $\leq 12$ genotypes, and in 13 compared to $\leq 12$ genotypes in the whole sample population and in Caucasians. In African-Americans $\leq 12$ genotypes had significantly higher UGT1A1 activity compared to either 13 or $\geq 14$ genotypes ($P=0.028$ and 0.016, respectively), but UGT1A1 activity was not significantly different between 13 and $\geq 14$ genotypes ($P=0.11$).

Figure 6:
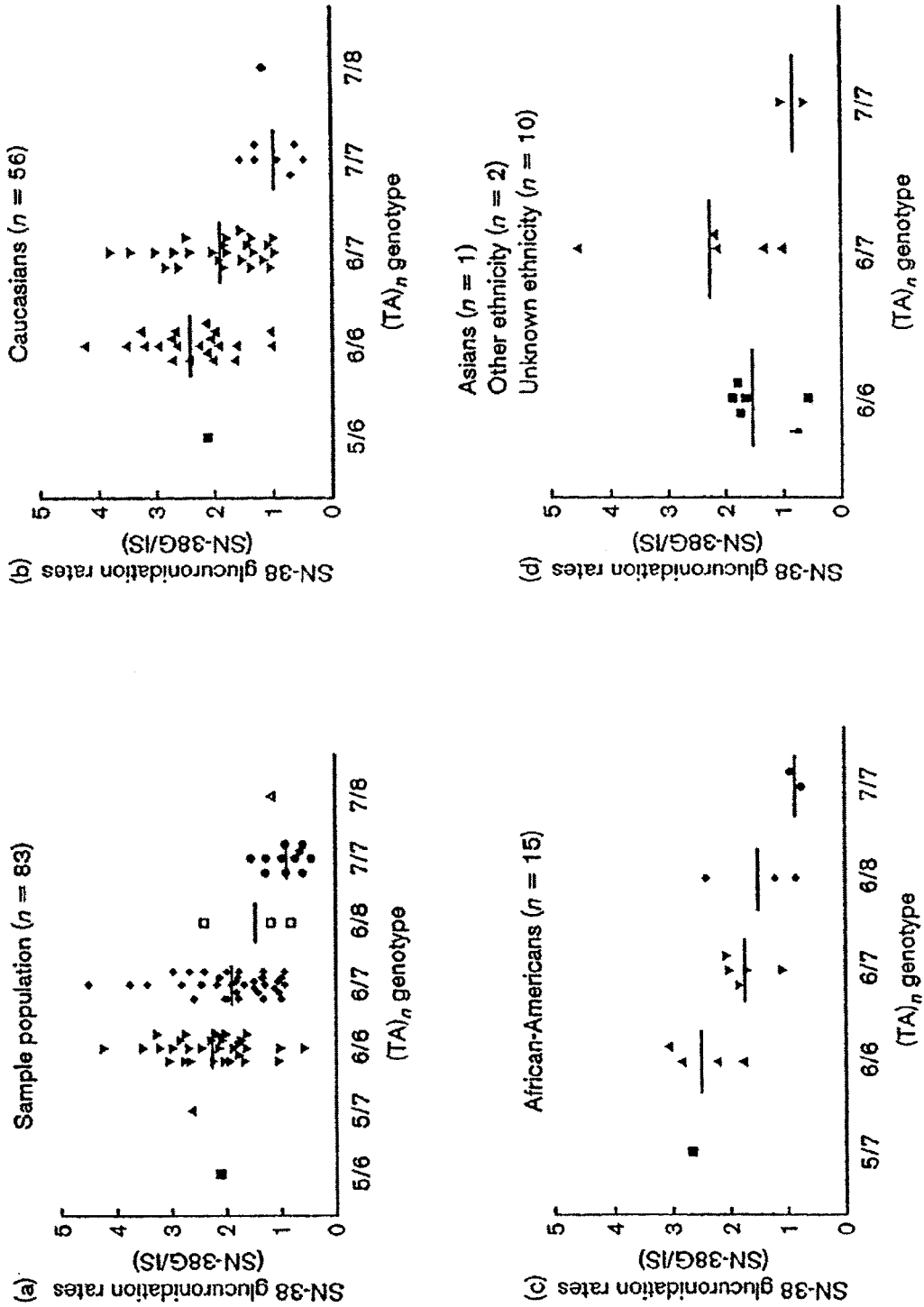
FIG. 6 $(TA)_n$ genotype-phenotype relationship in human livers.

In samples of Caucasian and African origin, SN-38 glucuronidation rate varies significantly across the haplotypes with a decreasing trend ($P<0.0001$, JT test) (FIG. 6). However, this apparent haplotype-phenotype correlation is likely to be due to the effect of the $(TA)_n$ polymorphism that is in linkage disequilibrium with the PBREM variants. Hence, the possible functional effects of the common $-3279G>T$ and $-3156G>A$ variants were investigated by comparing the SN-38 glucuronidation rates across genotypes that differed only by the variant being examined. Concerning the $-3279G>T$ variant, SN-38 glucuronidation was reduced in I/II pairs compared to I/I pairs among Caucasians, although without reaching statistical significance ($2.06\pm0.74$ versus $2.53\pm0.82$ SN-38G/IS, respectively) (Wilcoxon rank sum test, $P=0.18$). Concerning the $-3156G>A$ variant, although SN-38 glucuronidation is slightly reduced in MI compared to I/VI pairs, the difference is not statistically significant (Wilcoxon rank sum test, $P=0.64$).

5. Materials and methods for experiments described above a. Chemicals and Reagents

Exonuclease I and shrimp alkaline phosphatase (exo/SAP) was purchased from USB (Cleveland, Ohio, USA). ABI Big Dye terminator cycle-sequencing kit was purchased from Applied Biosystems (Foster City, Calif., USA). Primers for amplification, sequencing of the PBREM, and amplification of the $(TA)_n$ polymorphism were obtained from GibcoBRL (Invitrogen Co., Carlsbad, Calif., USA). SN-38 was kindly provided by Dr Kiyoshi Terada (Yakult Honsha Co., Ltd, Japan). Camptothecin, UDPGA, magnesium chloride, trizma base, potassium monohydrogen phosphate and 1-heptanesulfonic acid were purchased from Sigma-Aldrich (St. Louis, Mo., USA). Acetonitrile, tetrahydrofuran and hydrochloric acid were obtained from Fisher Scientific (Hanover, Ill., USA).

b. Human Livers

Normal human livers ($n=83$) were mainly obtained from Liver Tissue Procurement and Distribution System (National Institutes of Diabetes and Digestive and Kidney Diseases, Minneapolis, Minn.). DNA was isolated by using Qiagen RNA/DNA Maxi Kit (Qiagen Inc., Valencia, Calif., USA), and microsomes were isolated following differential centrifugation methods (Purba et al., 1987). DNA and microsomes were provided by the Liver Core Bank Facility (St. Jude Children's Research Hospital) of the Pharmacogenetics of Anticancer Agents Research (PAAR) Group. In order to identify livers in which enzyme degradation occurred, liver samples consistently comprised in the 10th percentile of UGT1A1, UGT1A9 and UGT2B7 activities were sought. UGT1A9 and UGT2B7 activities were measured using specific probes (data not shown) (Ramirez et al., 2002 and Innocenti, et al., 2001). Out of eight samples within the 10th percentile of UGT1A1, only one sample was comprised within the 10th percentile of activities of the other two enzyme activities. If different handling/storage of the liver or microsomal protein degradation occurred in that sample, this should not have affected the degree of phenotype/genotype correlation because the individual had a 7/7 genotype, and among the 7/7 genotype samples ($n=11$), it had the 4th lower value. Moreover, lack of correlation between UGT1A1 and UGT2B7 activities ($n=83$, $r=0.07$, $P=0.5$) shows that differences in tissue integrity and microsome stability have probably a mild influence (if any) on the UGT phenotype.

The ethnic composition of the 83 liver donors comprised: Caucasians 68%, African-Americans 18%, Asians 1%, others 2%. The percentage of samples of unknown ethnic origin was 12%.

c. Genotyping of (TA)n Polymorphism

In order to genotype the $(TA)_n$ polymorphism, approximately 40 ng of DNA was subjected to amplification by polymerase chain reaction (PCR). The amplification primers used have been previously described (Monaghan et al., 1996), where the sequence of the forward primer is 5'-GTCACGT-GACACAGTCAAAC-3' (SEQ ID NO:2) and that of the reverse primer is 5'-TTTGCTCCTGCCAGAGGTT-3' (SEQ ID NO:3). These primers flank the polymorphic TA locus in the promoter region of the UGT1A1 gene and amplify a 98 bp fragment when a $(TA)_6$ allele is present and a 100 by fragment when a $(TA)_7$ allele is present. In the presence of $(TA)_5$ and $(TA)_8$ alleles, 96 by and 102 by alleles are amplified. The reverse primer is labeled with a fluorescent dye at its 5'-end to permit visualization of the amplification product. The amplification reactions were performed in a 10 μl volume consisting of 1.5 mmol $MgCl_2$, 250 mmol dNTPs, 0.8 mmol of each primer and 0.5 U of Tag polymerase (Amplitaq Gold from Applied Biosystems). The polymerase was activated at 95° C. for 10 min and DNA amplified for 35 cycles at 95° C. for 30 sec, 55° C. for 30 sec and 72° C. for 30 sec, followed by a final extension at 72° C. for 10 min. Control DNAs from individuals known to have a 6/6, 6/7 and 7/7 genotype were included in the PCR analysis. PCR fragments were subjected to gel electrophoresis on an ABI 377 DNA analyzer (Applied Biosystems). Amplified products were diluted in a formamide and dextran blue loading buffer and 1 µl combined with 1 µl of size standard (GS-350 from Applied Biosystems), denatured at 95° C., and loaded onto a 6% denaturing polyacrylamide gel. Electrophoresis was performed for 3.5 hours following manufacturers recommendations. The Genescan and Genotyper software (version 3.7, Applied Biosystems) was used to analyze fragments for size determination.

d. Sequencing of PBREM

A 606 by region (−3641 to −3036) including PBREM was successfully PCR-amplified and sequenced in 81 of the 83 human liver DNAs and 22 of the 24 DNA samples from African-American individuals (Americans of African descent, born in the USA) included in the NIGMS HGCR Human VariationPanel (Coriell Institute for Medical Research, Camden, N.J., USA). The reference sequence shown in FIG. 4 is that deposited in the GenBank database (accession number AF313454). Amplification of the PCR product was performed in a 10 or 25-pl reaction volume using the following primers: 5'-CTGGGGATAAACATGGGATG-3' SEQ ID NO:4 (forward) and 5'-CACCACCACTTCTG-GAACCT-3' SEQ ID NO:5 (reverse). These primers were designed using Primer3 software (Rozen et al., 1998). PCR conditions were 2 min at 94° C., 32 or 33 cycles of a three-step cycling program (30 sec at 94° C., 30 sec at 66.8° C. and 1 min at 72° C.) and 72° C. for 3 min. Following exo/SAP cleanup of the PCR product, this amplicon was then sequenced in the forward and reverse directions using the amplification primers, Big Dye terminator chemistry, and run on an ABI 3700 (Applied Biosystems) following the manufacturer's protocol. Sequences were analyzed and individuals genotyped using the Poly-Phred software (Nickerson et al., 1997). To determine the ancestral state of the polymorphisms found in humans, the sequence was compared to that of baboon (accession number AC091778).

e. SN-38 Glucuronidation Assay in Human Liver Microsomes

Samples were phenotyped by using SN-38 as a substrate for UGT1A1. The incubation mixture consisted of 5 µmol SN-38, 10 mmol $MgCl_2$, 1 mg/ml microsomes, 0.025 mol Tris-HCl (pH 7.4) and 5 mmol UDP-GA. Samples were incubated for 30 min at 37° C. The reaction was stopped by the addition of methanol. These conditions were selected after previous optimization of the enzyme reaction (Iyer et al., 1998). Camptothecin (75 ng) was used as an internal standard. SN-38 glucuronidation was measured by HPLC (Hitachi Instruments Inc., San Jose, Calif., USA) with fluorescence detection (λ, excitation=355 nm, λ, emission=515 nm). A µBondapak™ $C_{18}$ column (3.9×300 mm, 10 µm; Waters Corp., Milford, Mass., USA) and µBondapak™ $C_{18}$ guardpak (Waters Corp.) were used. A mobile phase of Aug. 4, 1988 acetonitrile/tetra-hydrofuran/0.9 mmol sodium heptanedfonic acid in 50 mmol potassium dihydrogen phosphate (pH 4) was used during the first 7 min of the run. From 7.1-25 min, the eluent consisted of 30/70 acetonitrile/5 mmol sodium heptanesulfonic acid in 50 mmol potassium dihydrogen phosphate (pH 4). The flow rate was 0.9 ml/min. Retention times for SN-38G, SN-38 and camptothecin were 13.3, 18.4 and 19.3 min, respectively. SN-38 glucuronidation rates were reported as the ratios between SN-38 glucuronide (SN-38G) and internal standard (IS) peak heights. The intra-assay variability was determined by performing 10 incubations on the same day using a pool of human liver microsomes. The inter-assay variability was evaluated by incubating a pool of human liver microsomes in triplicate on three different days. The inter- and intra-assay variabilities were within 7%.

f. Statistical Analysis

The significance of linkage disequilibrium between pairs of polymorphic sites was assessed using genotypic data and a likelihood ratio test provided in ARLEQUIN, version 2 (Schneider et al., 2000). ARLEQUIN was also used to run a modified Markov-chain random walk algorithm to test for Hardy-Weinberg equilibrium. Next, multisite haplotypes were estimated using the program PHASE (Stephens et al., 2001). Because this program does not accept both bi-allelic and multi-allelic polymorphic sites, haplotypes were estimated only for individuals with either the $(TA)_6$ or $(TA)_7$ alleles.

Thirteen individuals were heterozygous for the $(TA)_5$ or $(TA)_8$ repeat, three of which were heterozygous only at the TA repeat and therefore unambiguous at the other sites. For the remaining 10 individuals, haplotypes were determined manually by assuming that the chromosome with the $(TA)_6$ or $(TA)_7$ allele contained a haplotype previously identified by the PHASE analysis. In one case, this method would have resulted in a new $(TA)_8$ haplotype. However, it is more likely that this individual would instead have a novel $(TA)_6$ haplotype (V), which is consistent with the observation that the $(TA)_6$ allele is found on multiple haplotypes, including other rare ones. An incorrect assignment would have little or no affect on the subsequent analyses because the novel haplotype only occurs once out of 103 individuals and not in a sample used in studies of correlation with phenotype.

The effective number of haplotypes was calculated as the reciprocal of the sum of the frequency squared. Diversity in $(TA)_6$ haplotypes in Caucasians and African-Americans, based on the numbers and frequencies of haplotypes and adjusted by sample size, was estimated by DnaSP version 3.53 (Rozas et al.) as well as their SDs. Statistical significance was assessed using a t-test as previously described (Nei, 1987). The chi-square test was used to analyze the differences in genotype/haplotype frequencies between Caucasians and African-Americans.

UGT1A1 activity was phenotyped by measuring SN-38 glucuronidation rates of each liver as the mean±SD of a single experiment performed in triplicate. The statistical analysis of the relationship between the $(TA)_6$ polymorphism and phenotype was planned to assess first the genotype effect on phenotype in the population sample (n=83) using the analysis of variance (ANOVA). If the genotype effect was statistically significant then, within each ethnic group, a test of trend across the genotypes was performed using the exact Jonkheerer-Terpstra (JT) test (Gibbons et al., 1992). Pairwise comparisons between two genotypes were performed using an exact one-sided Wilcoxon test. Moreover, trend analysis and pairwise comparisons were performed in genotypes expressed as the sum of TA repeats in both chromosomes (i.e., in samples with ≦12 (5/6, 6/6, 5/7), 13 (6/7) and ≦14 (7/7, 6/8, 7/8) TA repeat genotypes). Concerning the haplotype-phenotype relationship, two-sided exact Wilcoxon tests were used to compare the SN-38 glucuronidation rates between two haplotypes. SAS system (SAS Institute, Inc., Cary, N.C.) and StatXact-5 (CYTEL Software Corporation, Cambridge, Mass., USA) were used for statistical analysis. GraphPad software version 3.02 (GraphPad Software Inc., San Diego, Calif., USA) was used for graphical analysis.

II. Nucleic Acids

Certain embodiments of the present invention concern various nucleic acids, including promoters, amplification primers, oligonucleotide probes and other nucleic acid elements involved in the analysis of genomic DNA. In certain aspects, a nucleic acid comprises a wild-type, a mutant, or a polymorphic nucleic acid.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length. A "gene" refers to coding sequence of a gene product, as well as introns and the promoter of the gene product. In addition to the UGT1A1 gene, other regulatory regions such as enhancers for UGT1A1 are contemplated as nucleic acids for use with compositions and methods of the claimed invention.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss", a double stranded nucleic acid by the prefix "ds", and a triple stranded nucleic acid by the prefix "ts."

In particular aspects, a nucleic acid encodes a protein, polypeptide, or peptide. In certain embodiments, the present invention concerns novel compositions comprising at least one proteinaceous molecule. As used herein, a "proteinaceous molecule," "proteinaceous composition," "proteinaceous compound," "proteinaceous chain," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

1. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in European Patent 266,032, incorporated herein by reference, or via deoxynucleoside H-phosphonate intermediates as described by Froehler et al., 1986 and U.S. Pat. No. 5,705,629, each incorporated herein by reference. In the methods of the present invention, one or more oligonucleotide may be used. Various different mechanisms of oligonucleotide synthesis have been disclosed in for example, U.S. Pat. Nos. 4,659,774, 4,816,571, 5,141,813, 5,264,566, 4,959, 463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. No. 4,683,202 and U.S. Pat. No. 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

2. Purification of Nucleic Acids

A nucleic acid may be purified on polyacrylamide gels, cesium chloride centrifugation gradients, chromatography columns or by any other means known to one of ordinary skill in the art (see for example, Sambrook et al., 2001, incorporated herein by reference). In some aspects, a nucleic acid is a pharmacologically acceptable nucleic acid. Pharmacologically acceptable compositions are known to those of skill in the art, and are described herein.

In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

3. Nucleic Acid Segments

In certain embodiments, the nucleic acid is a nucleic acid segment. As used herein, the term "nucleic acid segment," are fragments of a nucleic acid, such as, for a non-limiting example, those that encode only part of a UGT1 gene locus or a UGT1A1 gene sequence. Thus, a "nucleic acid segment" may comprise any part of a gene sequence, including from about 2 nucleotides to the full length gene including promoter regions to the polyadenylation signal and any length that includes all the coding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

$$n \text{ to } n+y$$

where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

4. Nucleic Acid Complements

The present invention also encompasses a nucleic acid that is complementary to a nucleic acid. A nucleic acid is "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule. In preferred embodiments, a complement is a hybridization probe or amplification primer for the detection of a nucleic acid polymorphism.

As used herein, the term "complementary" or "complement" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. However, in some diagnostic or detection embodiments, completely complementary nucleic acids are preferred.

III. Nucleic Acid Detection

Some embodiments of the invention concern identifying polymorphisms in UGT1A1, correlating genotype or haplotype to phenotype, wherein the phenotype is lowered or altered UGT1A1 activity or expression, and then identifying such polymorphisms in patients who have or will be given irinotecan or related drugs or compounds. Thus, the present invention involves assays for identifying polymorphisms and other nucleic acid detection methods. Nucleic acids, therefore, have utility as probes or primers for embodiments involving nucleic acid hybridization. They may be used in diagnostic or screening methods of the present invention. Detection of nucleic acids encoding UGT1A1, as well as nucleic acids involved in the expression or stability of UGT1A1 polypeptides or transcripts, are encompassed by the invention. General methods of nucleic acid detection methods are provided below, followed by specific examples employed for the identification of polymorphisms, including single nucleotide polymorphisms (SNPs).

A. Hybridization

The use of a probe or primer of between 3, 4, 5, 6, 7, 8, 9, 10, 11, 12, 13, 14, or 15 and 50, 60, 70, 80, 90, or 100 nucleotides, preferably between 17 and 100 nucleotides in length, or in some aspects of the invention up to 1-2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting a specific polymorphism. It is generally appreciated that conditions can be rendered more stringent by the addition of increasing amounts of formamide. For example, under highly stringent conditions, hybridization to filter-bound DNA may be carried out in 0.5 M NaHPO$_4$, 7% sodium dodecyl sulfate (SDS), 1 mM EDTA at 65° C., and washing in 0.1×SSC/0.1% SDS at 68° C. (Ausubel et al., 1989).

Conditions may be rendered less stringent by increasing salt concentration and/or decreasing temperature. For example, a medium stringency condition could be provided by about 0.1 to 0.25M NaCl at temperatures of about 37° C. to about 55° C., while a low stringency condition could be provided by about 0.15M to about 0.9M salt, at temperatures ranging from about 20° C. to about 55° C. Under low stringent conditions, such as moderately stringent conditions the washing may be carried out for example in 0.2×SSC/0.1% SDS at 42° C. (Ausubel et al., 1989). Hybridization conditions can be readily manipulated depending on the desired results.

In other embodiments, hybridization may be achieved under conditions of, for example, 50 mM Tris-HCl (pH 8.3), 75 mM KCl, 3 mM MgCl$_2$, 1.0 mM dithiothreitol, at temperatures between approximately 20° C. to about 37° C. Other hybridization conditions utilized could include approximately 10 mM Tris-HCl (pH 8.3), 50 mM KCl, 1.5 mM MgCl$_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples. In other aspects, a particular nuclease cleavage site may be present and detection of a particular nucleotide sequence can be determined by the presence or absence of nucleic acid cleavage.

In general, it is envisioned that the probes or primers described herein will be useful as reagents in solution hybridization, as in PCR, for detection of expression or genotype of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849, 481, 5,849,486 and 5,851,772. The relevant portions of these and other references identified in this section of the Specification are incorporated herein by reference.

B. Amplification of Nucleic Acids

Nucleic acids used as a template for amplification may be isolated from cells, tissues or other samples according to standard methodologies (Sambrook et al., 2001). In certain embodiments, analysis is performed on whole cell or tissue homogenates or biological fluid samples with or without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to the UGT1 gene locus (Genbank accession AF279093), UGT1A1 gene and/or SEQ ID NO:1 or variants thereof, and fragments thereof are contacted with the template nucleic acid under conditions that permit selective hybridization. SEQ ID NO:1 set forth a nucleotide sequence that includes a majority of the UGT1A1 gene. SEQ ID NO:1 includes nucleotides 169,831 to 187,313 of the UGT1 gene locus with nucleotide 1645 of SEQ ID NO:1 corresponding to nucleotide −3565 from the transcriptional start of the UGT1A1 gene, thus the transcriptional start is located at nucleotide 5212 of SEQ ID NO:1. Depending upon the desired application, high stringency hybridization conditions may be selected that will only allow hybridization to sequences that are completely complementary to the primers. In other embodiments, hybridization may occur under reduced stringency to allow for amplification of nucleic acids that contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected, analyzed or quantified. In certain applications, the detection may be performed by visual means. In certain applications, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA) (described in further detail below), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, Great Britain Application 2 202 328, and in PCT Application PCT/US89/01025, each of which is incorporated herein by reference in its entirety. Qbeta Replicase, described in PCT Application PCT/US87/00880, may also be used as an amplification method in the present invention.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i.e., nick translation Other nucleic acid amplification procedures include transcription-based amplification systems (TAS), including nucleic acid sequence based amplification (NASBA) and 3SR (Kwoh et al., 1989; PCT Application WO 88/10315, incorporated herein by reference in their entirety). European Application 329 822 disclose a nucleic acid amplification process involving cyclically synthesizing single-stranded RNA ("ssRNA"), ssDNA, and double-stranded DNA (dsDNA), which may be used in accordance with the present invention.

PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990; Ohara et al., 1989).

C. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 2001). Separated amplification products may be cut out and eluted from the gel for further manipulation. Using low melting point agarose gels, the separated band may be removed by heating the gel, followed by extraction of the nucleic acid.

Separation of nucleic acids may also be effected by spin columns and/or chromatographic techniques known in art. There are many kinds of chromatography which may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized, with or without separation. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art (see Sambrook et al., 2001). One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

D. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

E. Specific Examples of SNP Screening Methods

Spontaneous mutations that arise during the course of evolution in the genomes of organisms are often not immediately transmitted throughout all of the members of the species, thereby creating polymorphic alleles that co-exist in the species populations. Often polymorphisms are the cause of genetic diseases. Several classes of polymorphisms have been identified. For example, variable nucleotide type polymorphisms (VNTRs), arise from spontaneous tandem duplications of di- or trinucleotide repeated motifs of nucleotides. If such variations alter the lengths of DNA fragments generated by restriction endonuclease cleavage, the variations are referred to as restriction fragment length polymorphisms (RFLPs). RFLPs are been widely used in human and animal genetic analyses.

Another class of polymorphisms are generated by the replacement of a single nucleotide. Such single nucleotide polymorphisms (SNPs) rarely result in changes in a restriction endonuclease site. Thus, SNPs are rarely detectable restriction fragment length analysis. SNPs are the most common genetic variations and occur once every 100 to 300 bases and several SNP mutations have been found that affect a single nucleotide in a protein-encoding gene in a manner sufficient to actually cause a genetic disease. SNP diseases are exemplified by hemophilia, sickle-cell anemia, hereditary hemochromatosis, late-onset alzheimer disease etc.

In context of the present invention, polymorphic mutations that affect the activity and/or levels of the UGT1A1 gene products, which are responsible for the glucuronidation of irinotecan and other chemotherapeutic and xenobiotic agents, will be determined by a series of screening methods. One set of screening methods is aimed at identifying SNPs that affect the inducibility, activity and/or level of the UGT1A1 gene products in in vitro or in vivo assays. The other set of screening methods will then be performed to screen an individual for the occurrence of the SNPs identified above. To do this, a sample (such as blood or other bodily fluid or tissue sample) will be taken from a patient for genotype analysis. The presence or absence of SNPs will determine the ability of the screened individuals to metabolize irinotecan and other chemotherapeutic agents that are metabolized by the UGT1A1 gene products. According to methods provided by the invention, these results will be used to adjust and/or alter the dose of irinotecan or other agent administered to an individual in order to reduce drug side effects.

SNPs can be the result of deletions, point mutations and insertions and in general any single base alteration, whatever the cause, can result in a SNP. The greater frequency of SNPs means that they can be more readily identified than the other classes of polymorphisms. The greater uniformity of their distribution permits the identification of SNPs "nearer" to a particular trait of interest. The combined effect of these two attributes makes SNPs extremely valuable. For example, if a particular trait (e.g., inability to efficiently metabolize irinotecan) reflects a mutation at a particular locus, then any polymorphism that is linked to the particular locus can be used to predict the probability that an individual will be exhibit that trait.

Several methods have been developed to screen polymorphisms and some examples are listed below. The reference of Kwok and Chen (2003) and Kwok (2001) provide overviews of some of these methods; both of these references are specifically incorporated by reference.

SNPs relating to glucuronidation of chemotherapeutic agents can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

i) DNA Sequencing

The most commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger, F., et al., 1975) or the "chemical degradation method," also known as the "Maxam-Gilbert method" (Maxam, A. M., et al., 1977). Sequencing in combination with genomic sequence-specific amplification technologies, such as the polymerase chain reaction may be utilized to facilitate the recovery of the desired genes (Mullis, K. et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

ii) Exonuclease Resistance

Other methods that can be employed to determine the identity of a nucleotide present at a polymorphic site utilize a specialized exonuclease-resistant nucleotide derivative (U.S. Pat. No. 4,656,127). A primer complementary to an allelic sequence immediately 3'- to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

iii) Microsequencing Methods

Several other primer-guided nucleotide incorporation procedures for assaying polymorphic sites in DNA have been described (Komher, J. S. et al., 1989; Sokolov, B. P., 1990; Syvanen 1990; Kuppuswamy et al., 1991; Prezant et al., 1992; Ugozzoll, L. et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

iv) Extension in Solution

French Patent 2,650,840 and PCT Application WO91/02087 discuss a solution-based method for determining the identity of the nucleotide of a polymorphic site. According to these methods, a primer complementary to allelic sequences immediately 3'- to a polymorphic site is used. The identity of the nucleotide of that site is determined using labeled dideoxynucleotide derivatives which are incorporated at the end of the primer if complementary to the nucleotide of the polymorphic site.

v) Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

vi) Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

vii) Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

viii) Other Methods to Detect SNPs

Several other specific methods for SNP detection and identification are presented below and may be used as such or with suitable modifications in conjunction with identifying polymorphisms of the UGT1A1 genes in the present invention. Several other methods are also described on the SNP web site of the NCBI at the website on the world wide web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter is referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to variant detector array (VDA) can be performed by a Affymetrix High Throughput Screening Center and analyzed with computerized software.

A method called Chip Assay uses PCR amplification of genomic segments by standard or long PCR protocols. Hybridization products are analyzed by VDA, Halushka et al., 1999, incorporated herein by reference. SNPs are generally classified as "Certain" or "Likely" based on computer analysis of hybridization patterns. By comparison to alternative detection methods such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using the following conditions: 200 ng DNA template, 0.5 µM each primer, 80 µM each of dCTP, dATP, dTTP and dGTP, 5% formamide, 1.5 mM $MgCl_2$, 0.5 U of Taq polymerase and 0.1 volume of the Taq buffer. Thermal cycling is performed and resulting PCR-products are analyzed by PCR-single strand conformation polymorphism (PCR-SSCP) analysis, under a variety of conditions, e.g., 5 or 10% polyacrylamide gel with 15% urea, with or without 5% glycerol. Electrophoresis is performed overnight. PCR-products that show mobility shifts are reamplified and sequenced to identify nucleotide variation.

In a method called CGAP-GAI (DEMIGLACE), sequence and alignment data (from a PHRAP.ace file), quality scores for the sequence base calls (from PHRED quality files), distance information (from PHYLIP dnadist and neighbour programs) and base-calling data (from PHRED '-d' switch) are loaded into memory. Sequences are aligned and examined for each vertical chunk ('slice') of the resulting assembly for disagreement. Any such slice is considered a candidate SNP (DEMIGLACE). A number of filters are used by DEMIGLACE to eliminate slices that are not likely to represent true polymorphisms. These include filters that: (i) exclude sequences in any given slice from SNP consideration where neighboring sequence quality scores drop 40% or more; (ii) exclude calls in which peak amplitude is below the fifteenth percentile of all base calls for that nucleotide type; (iii) disqualify regions of a sequence having a high number of disagreements with the consensus from participating in SNP calculations; (iv) removed from consideration any base call with an alternative call in which the peak takes up 25% or more of the area of the called peak; (v) exclude variations that occur in only one read direction. PHRED quality scores were converted into probability-of-error values for each nucleotide in the slice. Standard Baysian methods are used to calculate the posterior probability that there is evidence of nucleotide heterogeneity at a given location.

In a method called CU-RDF (RESEQ), PCR amplification is performed from DNA isolated from blood using specific primers for each SNP, and after typical cleanup protocols to remove unused primers and free nucleotides, direct sequencing using the same or nested primers.

In a method called DEBNICK (METHOD-B), a comparative analysis of clustered EST sequences is performed and confirmed by fluorescent-based DNA sequencing. In a related method, called DEBNICK (METHOD-C), comparative analysis of clustered EST sequences with phred quality >20 at the site of the mismatch, average phred quality >=20 over 5 bases 5'-FLANK and 3' to the SNP, no mismatches in 5 bases 5' and 3' to the SNP, at least two occurrences of each allele is performed and confirmed by examining traces.

In a method identified by ERO (RESEQ), new primers sets are designed for electronically published STSs and used to amplify DNA from 10 different mouse strains. The amplification product from each strain is then gel purified and sequenced using a standard dideoxy, cycle sequencing technique with $^{33}$P-labeled terminators. All the ddATP terminated reactions are then loaded in adjacent lanes of a sequencing gel followed by all of the ddGTP reactions and so on. SNPs are identified by visually scanning the radiographs.

In another method identified as ERO (RESEQ-HT), new primers sets are designed for electronically published murine DNA sequences and used to amplify DNA from 10 different mouse strains. The amplification product from each strain is prepared for sequencing by treating with Exonuclease I and Shrimp Alkaline Phosphatase. Sequencing is performed using ABI Prism Big Dye Terminator Ready Reaction Kit (Perkin-Elmer) and sequence samples are run on the 3700 DNA Analyzer (96 Capillary Sequencer).

FGU-CBT (SCA2-SNP) identifies a method where the region containing the SNP is PCR amplified using the primers SCA2-FP3 and SCA2-RP3. Approximately 100 ng of genomic DNA is amplified in a 50 ml reaction volume containing a final concentration of 5 mM Tris, 25 mM KCl, 0.75 mM $MgCl_2$, 0.05% gelatin, 20 µmol of each primer and 0.5 U of Taq DNA polymerase. Samples are denatured, annealed and extended and the PCR product is purified from a band cut out of the agarose gel using, for example, the QIAquick gel extraction kit (Qiagen) and is sequenced using dye terminator chemistry on an ABI Prism 377 automated DNA sequencer with the PCR primers.

In a method identified as JBLACK (SEQ/RESTRICT), two independent PCR reactions are performed with genomic DNA. Products from the first reaction are analyzed by sequencing, indicating a unique FspI restriction site. The mutation is confirmed in the product of the second PCR reaction by digesting with Fsp I.

In a method described as KWOK(1), SNPs are identified by comparing high quality genomic sequence data from four randomly chosen individuals by direct DNA sequencing of PCR products with dye-terminator chemistry (see Kwok et al., 1996). In a related method identified as KWOK (2) SNPs) are identified by comparing high quality genomic sequence data from overlapping large-insert clones such as bacterial artificial chromosomes (BACs) or P1-based artificial chromosomes (PACs). An STS containing this SNP is then developed and the existence of the SNP in various populations is confirmed by pooled DNA sequencing (see Taillon-Miller et al., 1998). In another similar method called KWOK(3), SNPs are identified by comparing high quality genomic sequence data from overlapping large-insert clones BACs or PACs. The SNPs found by this approach represent DNA sequence variations between the two donor chromosomes but the allele frequencies in the general population have not yet been determined. In method KWOK(5), SNPs are identified by comparing high quality genomic sequence data from a homozygous DNA sample and one or more pooled DNA samples by direct DNA sequencing of PCR products with dye-terminator chemistry. The STSs used are developed from sequence data found in publicly available databases. Specifically, these STSs are amplified by PCR against a complete hydatidiform mole (CHM) that has been shown to be homozygous at all loci and a pool of DNA samples from 80 CEPH parents (see Kwok et al., 1994).

In another such method, KWOK (OverlapSnpDetectionWithPolyBayes), SNPs are discovered by automated computer analysis of overlapping regions of large-insert human genomic clone sequences. For data acquisition, clone sequences are obtained directly from large-scale sequencing centers. This is necessary because base quality sequences are not present/available through GenBank. Raw data processing involves analyzed of clone sequences and accompanying base quality information for consistency. Finished ('base perfect', error rate lower than 1 in 10,000 bp) sequences with no associated base quality sequences are assigned a uniform base quality value of 40 (1 in 10,000 by error rate). Draft sequences without base quality values are rejected. Processed sequences are entered into a local database. A version of each sequence with known human repeats masked is also stored. Repeat masking is performed with the program "MASKERAID." Overlap detection: Putative overlaps are detected with the program "WUBLAST." Several filtering steps followed in order to eliminate false overlap detection results, i.e. similarities between a pair of clone sequences that arise due to sequence duplication as opposed to true overlap. Total length of overlap, overall percent similarity, number of sequence differences between nucleotides with high base quality value "high-quality mismatches." Results are also compared to results of restriction fragment mapping of genomic clones at Washington University Genome Sequencing Center, finisher's reports on overlaps, and results of the sequence contig building effort at the NCBI. SNP detection: Overlapping pairs of clone sequence are analyzed for candidate SNP sites with the 'POLYBAYES' SNP detection software. Sequence differences between the pair of sequences are scored for the probability of representing true sequence variation as opposed to sequencing error. This process requires the presence of base quality values for both sequences. High-scoring candidates are extracted. The search is restricted to substitution-type single base pair variations. Confidence score of candidate SNP is computed by the POLYBAYES software.

In method identified by KWOK (TaqMan assay), the Taq-Man assay is used to determine genotypes for 90 random individuals. In method identified by KYUGEN(Q1), DNA samples of indicated populations are pooled and analyzed by PLACE-SSCP. Peak heights of each allele in the pooled analysis are corrected by those in a heterozygote, and are subsequently used for calculation of allele frequencies. Allele frequencies higher than 10% are reliably quantified by this method. Allele frequency=0 (zero) means that the allele was found among individuals, but the corresponding peak is not seen in the examination of pool. Allele frequency=0-0.1 indicates that minor alleles are detected in the pool but the peaks are too low to reliably quantify.

In yet another method identified as KYUGEN (Method1), PCR products are post-labeled with fluorescent dyes and analyzed by an automated capillary electrophoresis system under SSCP conditions (PLACE-SSCP). Four or more individual DNAs are analyzed with or without two pooled DNA (Japanese pool and CEPH parents pool) in a series of experiments. Alleles are identified by visual inspection. Individual DNAs with different genotypes are sequenced and SNPs identified. Allele frequencies are estimated from peak heights in the pooled samples after correction of signal bias using peak heights in heterozygotes. For the PCR primers are tagged to have 5'-ATT or 5'-GTT at their ends for post-labeling of both strands. Samples of DNA (10 ng/ul) are amplified in reaction mixtures containing the buffer (10 mM Tris-HCl, pH 8.3 or 9.3, 50 mM KCl, 2.0 mM $MgCl_2$), 0.25 µM of each primer, 200 µM of each dNTP, and 0.025 units/µl of Taq DNA polymerase premixed with anti-Taq antibody. The two strands of PCR products are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. For the SSCP: an aliquot of fluorescently labeled PCR products and TAMRA-labeled internal markers are added to deionized formamide, and denatured. Electrophoresis is performed in a capillary using an ABI Prism 310 Genetic Analyzer. Genescan softwares (P-E Biosystems) are used for data collection and data processing. DNA of individuals (two to eleven) including those who showed different genotypes on SSCP are subjected for direct sequencing using big-dye terminator chemistry, on ABI Prism 310 sequencers. Multiple sequence trace files obtained from ABI Prism 310 are processed and aligned by Phred/Phrap and viewed using Consed viewer. SNPs are identified by PolyPhred software and visual inspection.

In yet another method identified as KYUGEN (Method2), individuals with different genotypes are searched by denaturing HPLC (DHPLC) or PLACE-SSCP (Inazuka et al., 1997) and their sequences are determined to identify SNPs. PCR is performed with primers tagged with 5'-ATT or 5'-GTT at their ends for post-labeling of both strands. DHPLC analysis is carried out using the WAVE DNA fragment analysis system (Transgenomic). PCR products are injected into DNASep column, and separated under the conditions determined using WAVEMaker program (Transgenomic). The two strands of PCR products that are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. SSCP followed by electrophoresis is performed in a capillary using an ABI Prism 310 Genetic Analyzer. Genescan softwares (P-E Biosystems). DNA of individuals including those who showed different genotypes on DHPLC or SSCP are subjected for direct sequencing using big-dye terminator chemistry, on ABI Prism 310 sequencer. Multiple sequence trace files obtained from ABI Prism 310 are processed and aligned by Phred/Phrap and viewed using Consed viewer. SNPs are identified by PolyPhred software and visual inspection. Trace chromatogram data of EST sequences in Unigene are processed with PHRED. To identify likely SNPs, single base mismatches are reported from multiple sequence alignments produced by the programs PHRAP, BRO and POA for each Unigene cluster. BRO corrected possible misreported EST orientations, while POA identified and analyzed non-linear alignment structures indicative of gene mixing/chimeras that might produce spurious SNPs. Bayesian inference is used to weigh evidence for true polymorphism versus sequencing error, misalignment or ambiguity, misclustering or chimeric EST sequences, assessing data such as raw chromatogram height, sharpness, overlap and spacing; sequencing error rates; context-sensitivity; cDNA library origin, etc.

In method identified as MARSHFIELD (Method-B), overlapping human DNA sequences which contained putative insertion/deletion polymorphisms are identified through searches of public databases. PCR primers which flanked each polymorphic site are selected from the consensus sequences. Primers are used to amplify individual or pooled human genomic DNA. Resulting PCR products are resolved on a denaturing polyacrylamide gel and a PhosphorImager is used to estimate allele frequencies from DNA pools.

IV. Pharmaceutical Compositions

Aqueous compositions may have an effective amount of irinotecan and/or an effective amount of a compound (second agent) that increases conjugative enzyme activity, as represented by a compound that increases the activity of the phase II conjugative enzyme, glucuronosyltransferase or that decreases biliary transport. Such compositions will generally be dissolved or dispersed in a pharmaceutically acceptable carrier or aqueous medium.

The phrases "pharmaceutically or pharmacologically acceptable" refer to molecular entities and compositions that do not produce an adverse, allergic or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

A. Parenteral Administration

The active compounds will often be formulated for parenteral administration, e.g., formulated for injection via the intravenous, intramuscular, sub-cutaneous, or even intraperitoneal routes. The preparation of an aqueous composition that contains irinotecan and a second agent as active ingredients will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, with even drug release capsules and the like being employable.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

B. Oral Administration

In certain embodiments, active compounds may be administered orally. This is contemplated for agents which are generally resistant, or have been rendered resistant, to proteolysis by digestive enzymes. Such compounds are contemplated to include all those compounds, or drugs, that are available in tablet form from the manufacturer and derivatives and analogues thereof.

For oral administration, the active compounds may be administered, for example, with an inert diluent or with an assimilable edible carrier, or they may be enclosed in hard or soft shell gelatin capsule, or compressed into tablets, or incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Upon formulation, the compounds will be administered in a manner compatible with the dosage formulation and in such amount as is therapeutically effective. The formulations are easily administered in a variety of dosage forms, such as those described below in specific examples.

C. Liposomes

In a particular embodiment, liposomal formulations are contemplated. Liposomal encapsulation of pharmaceutical agents prolongs their half-lives when compared to conventional drug delivery systems. Because larger quantities can be protectively packaged, this allow the opportunity for dose-intensity of agents so delivered to cells. This would be particularly attractive in the chemotherapy of cervical cancer if there were mechanisms to specifically enhance the cellular targeting of such liposomes to these cells.

"Liposome" is a generic term encompassing a variety of single and multilamellar lipid vehicles formed by the generation of enclosed lipid bilayers. Phospholipids are used for preparing the liposomes according to the present invention and can carry a net positive charge, a net negative charge or are neutral. Dicetyl phosphate can be employed to confer a negative charge on the liposomes, and stearylamine can be used to confer a positive charge on the liposomes. Liposomes are characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are cationic lipid-nucleic acid complexes, such as lipofectamine-nucleic acid complexes V. Kits Any of the compositions described herein may be comprised in a kit. In a non-limiting example, reagents for determining the genotype of one or both UGT1A1 genes are included in a kit. The kit may further include individual nucleic acids that can be amplify and/or detect particular nucleic acid sequences the UGT1A1 gene. It may also include one or more buffers, such as a DNA isolation bufffers, an amplification buffer or a hybridization buffer. The kit may also contain compounds and reagents to prepare DNA templates and isolate DNA from a sample. The kit may also include various labeling reagents and compounds.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit (labeling reagent and label may be packaged together), the kit also will generally contain a second, third or other additional container into which the additional components may be separately placed. However, various combinations of components may be comprised in a vial. The kits of the present invention also will typically include a means for containing the nucleic acids, and any other reagent containers in close confinement for commercial sale. Such containers may include injection or blow-molded plastic containers into which the desired vials are retained.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

A kit will also include instructions for employing the kit components as well the use of any other reagent not included in the kit. Instructions may include variations that can be implemented.

It is contemplated that such reagents are embodiments of kits of the invention. Such kits, however, are not limited to the particular items identified above and may include any reagent used directly or indirectly in the detection of polymorphisms in the UGT1A1 gene or the activity level of the UGT1A1 polypeptide.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Patient Selection

Patients with histologically confirmed solid tumors or lymphoma known to respond to irinotecan or for which no therapy of proven benefit exists were eligible to participate in this study. Other eligibility criteria included measurable disease by radiologic imaging or physical examination; age of at least 18 years; Karnofsky performance status of at least 70% (ambulatory and capable of self-care); and adequate organ function defined as absolute neutrophil count (ANC) $\geq 1500$ $\mu l^{-1}$, platelet count $\geq 100,000$ $\mu l^{-1}$, serum creatinine level $\leq 1.5$ mg/dl or creatinine clearance $\geq 60$ ml/min, AST and ALT levels <5 times the upper limit of normal, and conjugated bilirubin within normal limits. Patients must have been off previous anticancer therapy, including radiation therapy, for at least 4 weeks (6 weeks if the previous treatment included a nitrosourea or mitomycin C) and off colony stimulating factor for at least 2 weeks. Patients with a history of inflammatory bowel disease requiring therapy, chronic diarrheal syndrome, paralytic ileus, or organ or stem cell transplant were excluded from the study. Concurrent use of medications that may be substrates of the UGT1A1 enzyme or that may be inducers or inhibitors of UGT1A1 activity was not permitted. Pregnant and lactating women were also excluded from participation, and those with reproductive potential were required to use an effective contraceptive method if sexually active.

Treatment Protocol

Irinotecan was supplied by the National Cancer Institute (NCI) as an intravenous solution with concentration 20 mg/ml in either 2 ml or 5 ml vials. The amount of irinotecan to be administered was removed aseptically from the vial and added to 500 ml of 0.9% saline or 5% dextrose injection, USP. Thirty minutes after pretreatment with 20 mg intravenous ondansetron, irinotecan 350 mg/m$^2$ was administered as a 90 minute intravenous infusion once every 3 weeks—a standard dose and schedule. History, physical examination, complete blood count (CBC) with differential, serum chemistry profile (electrolytes, blood urea nitrogen, creatinine, glucose, albumin, alkaline phosphatase, GGTP, AST, ALT, total and conjugated bilirubin, uric acid, and lactate dehydrogenase), and coagulation profile (prothrombin time and partial thromboplastin time) were conducted prior to first treatment. Thereafter, history, physical examination, and toxicity assessment were conducted on day 1 of each cycle unless treatment-related toxicity required more frequent follow up. CBC and serum chemistry profile were obtained weekly throughout treatment, though CBCs were obtained 3 times per week with the appearance of grade 3 or 4 neutropenia or thrombocytopenia. Toxicity assessment was done according to the NCI common toxicity criteria, version 2.0 (website: ctep.cancer.gov). Objective tumor assessment by appropriate radiographic imaging was performed prior to starting therapy and after every 2 cycles.

Toxicity Management and Dose Modification

For patients who experienced diarrhea, abdominal pain, or diaphoresis within 24 hours of irinotecan administration, 0.25 mg to 1 mg of intravenous atropine was considered. Delayed diarrhea, defined as diarrhea occurring more than 24 hours after irinotecan administration, was treated promptly with loperamide 4 mg at the onset and then with 2 mg every 2 hours until the patient was diarrhea-free for at least 12 hours. For patients who failed loperamide therapy, diphenoxylate, octreotide, and tincture of opium were sequentially added as needed. Patients were instructed to aggressively hydrate orally and were admitted to the hospital for intravenous electrolyte and fluid replacement when necessary. A new course of therapy was not started until the ANC recovered to at least 1500 the platelet count recovered to at least 100,000 µl$^{-1}$, and treatment-related diarrhea fully resolved. Patients with grade 3 or 4 toxicities of any kind were dose-reduced by 50 mg/m$^2$ for subsequent cycles.

Sample Collection

Prior to the first irinotecan infusion, venous blood (4.5 ml) for genotyping was collected in purple top Vacutainer® tubes containing EDTA (Becton, Dickinson, and Company, Franklin Lakes, N.J.) and stored at –80° C. for no more than 5 days prior to analysis. Venous blood for pharmacokinetic analysis was collected on day 1 of cycle 1 for pharmacokinetic analysis. Samples of 7 ml were collected into green top sodium heparinized Vacutainer® tubes prior to the infusion; 30, 60, and 90 minutes during the infusion; and 10, 20, 30, 45, and 60 minutes and 1.5, 2, 4, 6, 12, and 24 hours after the infusion. Samples were centrifuged (2500 rpm, 20 min, 4° C.) and the plasma was immediately separated, transferred as two aliquots into storage tubes, frozen at –80° C. until analysis.

UGT1A1 Genotyping Assays

The variants typed in this study are listed in Table 1. The UGT1A1 (TA)nTAA polymorphism was genotyped by PCR and product sizing as previously described (Te et al., 2000). Alleles with 6 TA repeats resulted in a 98 by fragment while alleles with 7 TA repeats resulted in a 100 by fragment. Alleles with 5 TA and 8 TA repeats resulted in 96 by and 102 by fragments respectively. Alleles with 5, 6, 7, and 8 TA repeats are reported as (TA)n and genotypes are assigned based upon the number of TA repeats in each allele, i.e., 6/6, 6/7, 7/7, 6/8, et cetera.

The variants in the 5' upstream region (–3279G>T and –3156G>A) and in exon 1 [21]G>A (G71R) and 686C>A (P229Q)] were genotyped by single base extension (SBE) and separated on a denaturing high performance liquid chromatography (DHPLC) system (Devaney et al., 2001). Genotyping of the –3279G>T and –3156G>A variants was performed by PCR amplification of a 333 by fragment in the UGT1A1 5' upstream region that contains both variants. The PCR primers used were: 5'-ACC TCT AGT TAC ATA ACC TGA A-3' (SEQ ID NO. 6) (forward primer) and 5'-AAT AAA CCC GAC CTC ACC AC-3' (SEQ ID NO. 7) (reverse primer). PCRs were performed in a 15 µl volume containing 125 nM each primer, 2.5 mM MgCl$_2$, 50 µM each dNTP and 0.375 U of AmpliTaq Gold polymerase (Applied Biosystems) in the buffer provided by the manufacturer. PCR cycling conditions were for 40 cycles at 95° C. for 15 s, 58° C. for 15 s and 72° C. for 30 s in a 9600 thermal cycler (Applied Biosystems). PCR amplified products were purified using shrimp alkaline phosphatase and exonuclease I by incubating at 37° C. for 45 min prior to the SBE reaction. SBE reactions were performed in duplex for genotyping of both variants in 10 µl volumes containing 1 µM of extension primer (5'-GCC AAG GGT AGA GTT CAG T-3' (SEQ ID NO. 8) for –3279G>T and 5'-GAC CCC AGC CCA CCT GTC-3' (SEQ ID NO. 9) for –3156G>A), 250 µM each ddNTP and 1.25 U thermosequenase (Amersham Pharmacia Biotech). Reactions were cycled at 96° C. for 30 s, 55° C. for 30 s and 60° C. for 30 s for 60 cycles. Separation of the SBE products was performed on a WAVE 3500HT DHPLC system (Transgenomic Inc) at 70° C. after denaturation of the samples. The flow rate used was 1.5 ml/min and the run time for each sample was 2.5 min. The gradient used for elution of the SBE products was created by the software based on the length of the extended product and was adjusted from 24% to 34% buffer B over 2 min (buffer B contains 25% acetonitrile). Extended products were eluted in the order of C<G<T<A which is dependent on the hydrophobicity differences of the four bases.

Genotyping of the 211G>A and 686C>A exon 1 variants was performed by PCR amplification of a 774 by fragment that encompasses both variants. The PCR primers used were: 5'-ATG CTG GGA AGA TAC TGT TG-3' (SEQ ID NO. 10) (forward primer) and 5'-TTT GGT GAA GGC AGT TGA TT-3' (SEQ ID NO. 11) (reverse primer). PCRs were performed in a 15 µl, 1 volume containing 125 nM each primer, 2.5 mM MgCl$_2$, 100 µM each dNTP and 0.375 U of AmpliTaq Gold polymerase (Applied Biosystems) in the buffer provided by the manufacturer. PCR cycling conditions were for 40 cycles at 95° C. for 15 s, 55° C. for 15 s and 72° C. for 45 s in a 9600 thermal cycler (Applied Biosystems). PCR purification was performed as described above and the SBE reactions were performed in 10 ul volumes containing 1 μM of each extension primer (5'-GTC TTC AAG GTG TAA AAT GCT C-3' (SEQ ID NO. 12) for 211G>A or the 5'-GTG CGA CGT GGT TTA TTC CC-3' (SEQ ID NO. 13) for 686C>A) using the conditions described above. For separation on the DHPLC system, a flow rate of 1.5 ml/min and a run time of 3 min was used for each sample. The gradient used for elution of the SBE products was created by the WAVE software based on the length of the extended product and was adjusted from 25.6% to 38.1% buffer B over 2.5 min.

Pharmacokinetic Analysis

Plasma concentrations of irinotecan and its metabolites were determined as previously published (Iyer et al., 2001). Pharmacokinetic parameters for irinotecan, SN-38, and SN-38G were calculated using standard non-compartmental methods with WinNonlin 2.0 (Pharsight Corporation, Mountain View, Calif.). The area under the plasma concentration-time curve (AUC) from time zero to the last measured concentration of irinotecan and metabolites was determined by the linear trapezoidal method. The glucuronidation ratio was expressed as the ratio of the SN-38G AUC over SN-38 AUC.

Statistical Analysis

The study was originally designed to prospectively investigate the relationship between genetic variation in the UGT1A1 promoter and grade 3-4 diarrhea. Results from clinical trials using the 350 mg/m2 every 3 weeks schedule suggested a 20 to 35% frequency of diarrhea (ref). Based on previously published data, a single-gene Mendelian model implied that 16% of patients would have the 7/7 genotype, 48% would have the 6/7 genotype, and 36% would have the 6/6 genotype. A sample size of 60 would have had power of 0.8 at $\alpha$=0.05 to detect a linear trend in the proportion of patients within each genotype experiencing grade 3-4 diarrhea defined by 60% of 7/7 patients, 30% of 6/7 patients, and 10% of 6/6 patients.

However, due to lower than expected frequency of grade 3-4 diarrhea (see below), the analyses were instead focused on the frequency of grade 4 neutropenia (ANC<500 $\mu l^{-1}$). Nonparametric trend tests were used to investigate how the genotype is related to pharmacokinetic parameters, pretreatment bilirubin levels and ANC nadir. The relationship between genotype and grade 4 neutropenia was assessed by the use of Fisher's exact test and calculation of the relative risks. Univariate regression analyses were performed to identify the potential predictors of ANC nadir. They were performed on the log scale for ANC to reduce skewness in the residuals. The pretreatment variables were also considered jointly via analysis of covariance (ANCOVA) models in order to identify the pretreatment measurements that can predict ln(ANC nadir). A different ANCOVA model simultaneously considering the pre- and post-treatment variables was used to explore the mechanism through which variability in UGT1A1 status might affect the ANC nadir.

Example 2

Role of −3156G>A of UGT1A1 in Irinotecan Toxicity

Patient Characteristics

Sixty-six patients were enrolled in the study (Table 2). Blood was mistakenly not drawn for DNA extraction in one patient and genotype information is available in 65 patients. Sixty-three patients were assessable for toxicity as 3 patients (one 6/6, one 6/7, one 7/8) missed scheduled blood tests and/or physician appointments. Sixty patients are assessable for tumor response, as 6 of them were removed from the study before radiological assessment of tumor response. All the patients received prior chemotherapy regimens. Thirty-five of them received additional prior radiotherapy.

Allele and Genotype Frequencies

The TA indel allele frequencies were: $TA_6$=0.68, $TA_7$=0.29, $TA_8$=0.02, $TA_5$=0.01. The $TA_5$ and $TA_8$ alleles occurred exclusively in Black patients (one with 5/6, two patients with 6/8, and one patient with 7/8 genotype). −3279T and −3156A alleles had a frequency of 0.55 and 0.26, respectively.

Table 3 shows the frequencies of promoter haplotypes comprising −3279, −3156, and the TA indel, based upon our previous publication on their linkage disequilibrium (Innocenti et al., 2002). The frequency of the haplotype pairs is shown in table 4. No exon 1 variants (211G>A and 686C>A) were detected in this patient population.

Toxicity Prevalence, Relative Risk, Genetic Test.

Toxicity of diarrhea and neutropenia refer to events observed during cycle 1 of treatment. The frequency of grade 4 neutropenia was 9.5%. Grade 4 neutropenia was much more common in patients with genotype 7/7 (3/6, 50%) compared to patients with 6/7 genotype (3/24, 12.5%) and 6/6 genotype (0/30, 0%) (p=0.001, Fisher's exact test). Nonparametric trend analysis revealed that the TA indel polymorphism is significantly correlated to ln(ANC nadir) (7/7<6/7<6/6, z=−2.35, p=0.02) (FIG. 1).

Because the −3156G>A variant distinguishes between two different haplotypes in the $TA_7$ individuals, the relative risk of grade 4 neutropenia was analyzed for the −3156 AA genotype (versus AG and GG combined) and 7/7 genotype (versus 5/6, 6/6, 6/7 and 6/8 combined). A higher relative risk was found in patients with −3156 AA genotype (14.0, 95% CI 2.1-36.7) compared to patients with 7/7 genotype (9.3, 95% CI 1.7-40.7, n=63). Moreover, the predictive power of a genetic test in patients receiving irinotecan was evaluated for both the TA indel and the −3156 variant (Table 5). The predictive power of either 7/7 or −3156 AA genotypes for grade 4 neutropenia was evaluated. In addition, the predictive power of either 6/6 or −3156 GG genotypes was evaluated in relation to the absence of grade 4 neutropenia (i.e., grade 0-3). In this comparison, the two 6/8 patients were regarded as either 6/6 or 6/7 genotypes in order to assess whether patients with the $TA_8$ allele might be a confounding factor for the results of the genetic test.

While this study was originally conceived to examine the relationship between UGT1A1 genotype and severity of diarrhea, the frequency of grade 3 diarrhea in our patients was only 5% (n=3), with no instances of grade 4 diarrhea. None of the three patients with grade 3 diarrhea were 6/6 (2 6/7 and one 7/7 genotypes). Concerning the diarrhea events in patients with the $TA_8$ allele (two 6/8 and one 7/8), only a grade 1 event was reported in one 6/8 patient. The low frequency of severe diarrhea did not allow any formal statistical analysis.

Total Bilirubin: Correlation with TA Indel Genotype and Toxicity

Figure 5:
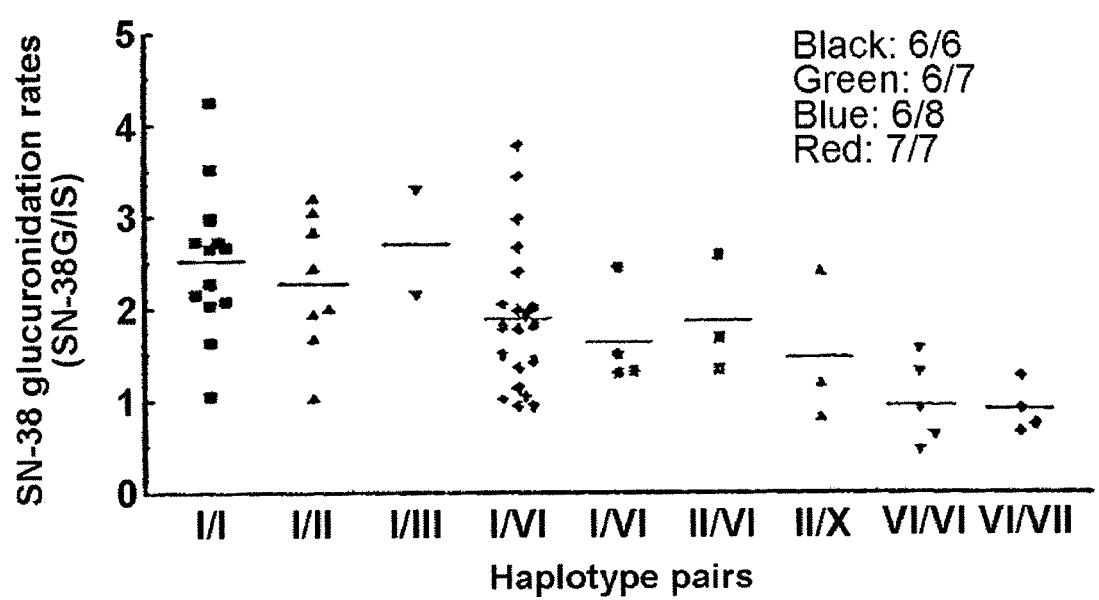
FIG. 5 Haplotype-phenotype relationships in human livers of Caucasian and African-Americans.

Pretreatment total bilirubin levels were obtained in all patients (0.5±0.22 mg/dl, mean±SD, n=66). As is shown in FIG. 5, total bilirubin levels were significantly correlated with the TA indel polymorphism (nonparametric trend analysis, 7/7>6/7>6/6, z=2.88, p<0.01). Total bilirubin levels were significantly higher in 7/7 patients compared to 6/6 and 6/7 patients combined (0.80±0.29 and 0.48±0.19 mg/dl, respectively, p=0.0003). Concerning the distribution of the −3156 genotypes withing each TA indel genotype group, in the 6/7 genotype group, the three patients with GG genotype had low bilirubin levels of 0.3-0.4 mg/dl. Similarly, the two patients with 6/8 and GG genotypes had low levels of bilirubin of 0.2-0.3 mg/dl. The one patient with GA genotype in the 7/7 group has a bilirubin level of 0.6 mg/dl, which is in the low range for this genotype group. The 7/8 patient did not have markedly elevated levels of total bilirubin as would be expected if the $TA_8$ allele resulted in decreased glucuronidation.

In addition, the −3156 and the TA indel variants were correlated with total bilirubin by multiple regression analysis. The AA genotype showed a slightly better correlation ($r^2=0.28$, $p<0.0001$) compared to 7/7 genotype, either when the $TA_8$ alleles were regarded as $TA_6$ ($r^2=0.23$, $p=0.002$) or $TA_7$ ($r^2=0.20$, $p=0.0009$). The other common variant −3279G>T had no significant association with total bilirubin (data not shown).

Figure 3:
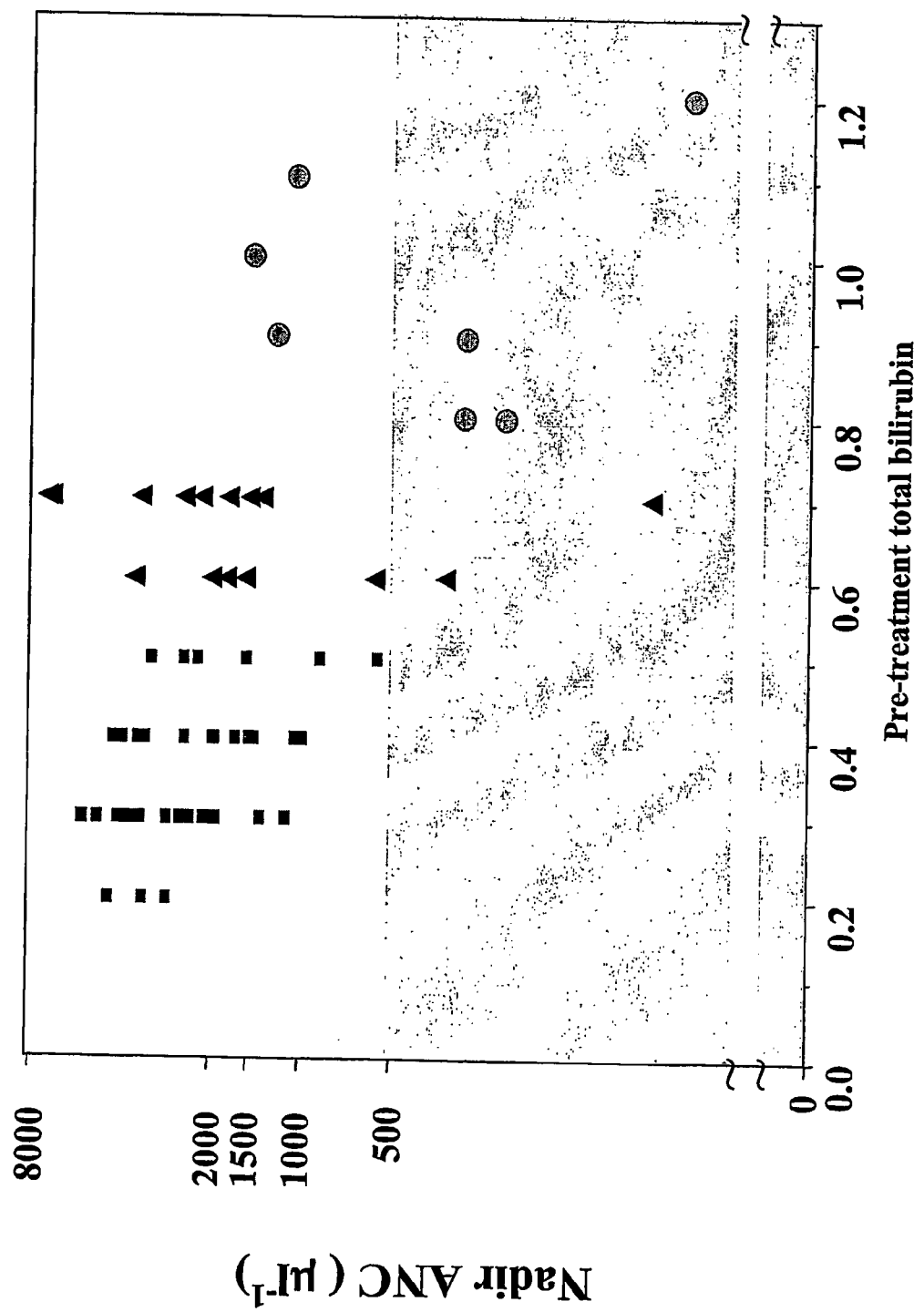
FIG. 3. Correlation between ln(ANC nadir) and pretreatment total bilirubin levels. Patients with bilirubin levels less than 0.6 mg/dl are depicted in squares. Those with bilirubin levels higher than 0.7 mg/dl are depicted in circles.

It was also analyzed whether pre-treatment bilirubin would correlate with neutropenia. Significantly higher bilirubin levels were observed in patients with grade 4 neutropenia ($0.83\pm0.21$ mg/dl) compared to those without grade 4 neutropenia ($0.47\pm0.20$ mg/dl) ($p=0.0001$) (FIG. 3). No cases of grade 4 neutropenia were reported in patients with bilirubin levels less than 0.6 mg/dl. Out of the 7 patients with total bilirubin higher then 0.7 mg/dl, 4 of them had grade 4 neutropenia.

Correlation Between TA Indel Genotype and PK Parameters

Table 6 describes the pharmacokinetic parameters of irinotecan and its metabolites stratified by 6/6, 6/7, and 7/7 genotypes. SN-38 AUC increases while increasing the number of $TA_7$ alleles (nonparametric trend analysis, 7/7>6/7>6/6, $z=2.13$, $p=0.03$). Conversely, glucuronidation ratios (SN-38G/SN-38 AUC ratios) were reduced while increasing the number of $TA_7$ alleles, (nonparametric trend analysis, 6/6>6/7>7/7, $z=−2.16$, $p=0.03$). No significant trend was found for irinotecan and SN-38G AUCs ($p>0.05$).

Regression Analysis

We sought to understand the impact of both pharmacokinetic variability and pre-treatment (including genotype) variables on variability in neutropenia. Instead of the TA indel genotype, the −3156 variant was used because 1) the −3156 genotype was better correlated with the risk of grade 4 neutropenia and 2) −3156 better reflected the UGT1A1 status of patients, based upon the data on the correlation with total bilirubin. Univariate regression analyses of ANC nadir selected SN-38 AUC, total bilirubin and −3156 genotype as the three best independent variables (Table 7). Gender showed a non-significant correlation with ANC nadir but it was included in further modeling because of possible gender differences in glucuronidation. Other variables did not show any correlation.

Multivariate Analyses

Several multivariate predictive ANCOVA models were considered to identify the pretreatment measurements that predict ln(ANC nadir). The final model ($r^2=0.41$) was selected by backward elimination from table 7 and is presented table 8. Pretreatment bilirubin level is found to be very significant and negatively related to ln(ANC nadir). Gender and −3156 genotype are found to be marginally significant after adjusting for the total bilirubin level. Ln(ANC nadir) is found to have a lower value in women, and it decreases with increasing number of $(TA)_7$ alleles (6/6>6/7>7/7). Other factors, such as ethnicity, number of prior regimens, performance status, and ln(pretreatment ANC) are not found to be significant predictors of ln(ANC nadir) after adjusting for −3156 genotype, gender and total bilirubin.

After determining the predictive model using pre-treatment variables, the post-treatment measurements of irinotecan AUC, SN-38 AUC, SN-38G AUC, and glucuronidation ratio were added to the model as independent variables with the intention of determining the possible mechanism of how the variability in UGT1A1 status affects ln(ANC nadir). The final model selected through backward elimination ($r^2=0.5141$) which best predicts ln(ANC nadir) includes genotype and SN-38 AUC ($p<0.001$) (table 9).

Toxic Death and Response

One toxic death was reported, as the patient died of neutropenia-related sepsis. He was admitted to the hospital on day 7 of cycle 1 with fever and an no neutrophils detected (white blood cell count of 100 $\mu l^{-1}$). He was empirically treated with ceftazadime, tobramycin, and fluconazole, though no infectious source was ever identified. Despite support with granulocyte colony stimulating factor, the patient remained neutropenic, became septic, and died on day 11. He had 7/7 genotype and the highest level of pretreatment total bilirubin observed in these patients (1.2 mg/dl).

Concerning the response rates in this trial, 3 objective responses were observed. Two patients achieved a partial response (one with colorectal and the other with head and neck cancer) and had a 6/7 genotype. One colorectal cancer patient achieved a complete response and had a 6/6 genotype.

Tables

TABLE 1

UGT1A1 variants typed in this study. Positions indicated are from the first base of the UGT1A1 start site in the UGT1A cluster reference sequence (AF297093).

| Nucleotide change | Amino acid change | Exon |
| --- | --- | --- |
| −3156G > A | — | Promoter |
| −3279G > T | — | Promoter |
| TA indel | — | Promoter |
| 211G > A | G71R | 1 |
| 686C > A | P229Q | 1 |

TABLE 2

Patient characteristics

| Patients | No. of patients |
| --- | --- |
| Entered | 66 |
| Assessable for toxicity | 63 |
| Assessable for response | 60 |
| Sex | |
| Male | 39 |
| Female | 27 |
| Age, median (range) | 60 (34-85) |
| Ethnicity | |
| White | 50 |
| Black | 10 |
| Hispanic | 4 |
| Pacific Islander | 1 |
| Asian | 1 |
| Performance Status | |
| 100% | 18 |
| 90% | 31 |
| 80% | 10 |
| 70% | 17 |

TABLE 2-continued

Patient characteristics

| | No. of patients |
|---|---|
| Tumor type | |
| Colorectal | 10 |
| Gastroesophageal | 14 |
| Head and Neck | 5 |
| Liver | 2 |
| Lung | 19 |
| Pancreas | 3 |
| Unknown Primary | 4 |
| Others | 9 |
| Prior Radiotherapy | 35 |

TABLE 3

Frequency of UGT1A1 promoter haplotypes.

| −3279G > T | −3156G > A | TA indel | Frequency |
|---|---|---|---|
| T | G | 6 | 0.55 |
| G | G | 6 | 0.13 |
| G | A | 7 | 0.25 |
| G | G | 7 | 0.03 |
| G | G | 8 | 0.02 |
| G | G | 5 | 0.01 |

TABLE 4

Frequency of haplotype pairs. The haplotypes reflect the change of −3279, −3156, and the TA indel variants, such as the first base refers to −3279 variants, the second to −3156 variant and the number refers to the number of TA repeats.

| Haplotype pairs | Frequency |
|---|---|
| TG6/TG6 | 0.28 |
| TG6/GA7 | 0.28 |
| TG6/GG6 | 0.18 |
| GA7/GA7 | 0.08 |
| GG6/TA7 | 0.06 |
| TG6/GG7 | 0.05 |
| TG6/GG8 | 0.02 |
| GG6/GG8 | 0.02 |
| GG5/TG6 | 0.02 |
| GA7/GG8 | 0.02 |

TABLE 5

Genetic tests for the TA indel and −3156 genotypes. Data are shown with 95% CI in parenthesis. The patient with 5/6 genotype was regarded as having a 6/6 genotype.

| | Sensitivity | Specificity | PPV | NPV |
|---|---|---|---|---|
| 7/7, grade 4 | 0.50 (0.19-0.81) | 0.95 (0.85-0.98) | 0.50 (0.19-0.81) | 0.95 (0.85-0.98) |
| −3156 AA, grade 4 | 0.50 (0.19-0.81) | 0.96 (0.88-0.99) | 0.60 (0.23-0.92) | 0.95 (0.86-0.98) |
| 6/6, grade 0-3, 6/8 = 6/6 | 0.57 (0.44-0.69) | 1.00 (0.61-1.00) | 1.00 (0.89-1.00) | 0.20 (0.10-0.37) |
| 6/6, grade 0-3, 6/8 = 6/7 | 0.54 (0.41-0.66) | 1.00 (0.61-1.00) | 1.00 (0.89-1.00) | 0.19 (0.09-0.35) |
| −3156 GG, grade 0-3 | 0.63 (0.49-0.74) | 1.00 (0.61-1.00) | 1.00 (0.90-1.00) | 0.22 (0.11-0.41) |

PPV, positive predictive value.

NPV, negative predicted value.

TABLE 6

Pharmacokinetic parameters and by 6/6, 6/7, and 7/7 TA indel genotypes. Data expressed as mean (standard deviation).

| TA indel genotype | No. of patients | Irinotecan AUC (ng*h/ml) | SN-38[a] AUC (ng*h/ml) | SN-38G AUC (ng*h/ml) | Glucuronidation Ratio[b] (SN-38G AUC/SN-38 AUC) |
|---|---|---|---|---|---|
| 6/6 | 30 | 24412.8 (7691.6) | 335.9 (167.7) | 1954.2 (1361.1) | 6.52 (3.98) |
| 6/7 | 25 | 26085.5 (10814.2) | 458.4 (379.8) | 1887.9 (1682.5) | 5.55 (4.79) |
| 7/7 | 6 | 25432.9 (6694.9) | 542.0 (195.3) | 1819.1 (1249.8) | 3.59 (2.81) |

[a] 6/6 < 6/7 < 7/7, z = 2.13, p = 0.03, non-parametric trend analysis.

[b] 6/6 > 6/7 > 7/7, z = −2.16, p = 0.03, non-parametric trend analysis.

TABLE 7

Univariate analysis of ln(ANC nadir).

| Independent Variable | $r^2$ | p |
|---|---|---|
| SN-38 AUC | 0.3523 | <0.0001 |
| Pre-treatment total bilirubin | 0.2979 | <0.0001 |
| −3156 genotype | 0.2413 | 0.0003 |
| Irinotecan AUC | 0.1273 | 0.0041 |
| Glucuronidation ratio | 0.1171 | 0.0060 |
| Gender | 0.0445 | 0.0971 |
| SN-38G AUC | 0.0411 | 0.1109 |
| Age ≧70 | 0.0242 | 0.2231 |
| White ethnicity | 0.0128 | 0.3764 |
| Ln (pre-treatment ANC) | 0.0000 | 0.9749 |
| Performance status | 0.0016 | 0.9923 |

TABLE 8

ANCOVA for the final predictive model of ln(ANC nadir) using pre-treatment variables. The overall model shows an $r^2$ value of 0.4048 (p < 0.0001).

| | Coefficient | SE | p-value |
|---|---|---|---|
| Intercept | 8.1885 | 0.2767 | <0.001 |
| Genotype | | | |
| AA vs. GG + GA | −0.9401 | 0.3986 | 0.022 |

TABLE 8-continued

ANCOVA for the final predictive model of ln(ANC nadir) using pre-treatment variables. The overall model shows an $r^2$ value of 0.4048 ($p < 0.0001$).

| | Coefficient | SE | p-value |
|---|---|---|---|
| Gender | | | |
| Males vs. Females | 0.4323 | 0.2001 | 0.035 |
| Total Bilirubin | −1.8452 | 0.4816 | <0.001 |

SE, standard error

TABLE 9

ANCOVA for the final predictive model of ln(ANC nadir) using pre-treatment and post-treatment variables. The overall model shows an $r^2$ value of 0.5128 ($p < 0.0001$).

| | Coefficient | SE | p-value |
|---|---|---|---|
| Intercept | 8.3111 | 0.1517 | <0.001 |
| Genotype | | | |
| AA vs. GG + GA | −1.3798 | 0.3234 | <0.001 |
| SN-38 AUC | −0.0019 | 0.0003 | <0.001 |

SE, standard error

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference.

Rougier et al., Lancet., 351(9117):1677-1681, 1998.
Cunningham et al., Lancet., 352(9138):1413-1418, 1998.
Saltz et al., N. Engl. J. Med., 343(13):905-914, 2000.
Rothenberg et al., J. Clin. Oncol., 19(18):3801-3807, 2001.
Rothenberg et al., J. Clin. Oncol., 11(11):2194-21204, 1993.
Fuchs et al., J. Clin. Oncol., 21(5):807-814, 1993.
Vanhoefer et al., J. Clin. Oncol., 19(5):1501-18, 2001.
Ratain et al., J. Clin. Oncol., 20(1):7-8, 2002.
Beutler et al., Proc. Natl. Acad. Sci. USA, 95(14):8170-8174, 1998.
Te et al., Transplantation, 69:1882, 2000.
Devaney et al., Anal. Chem., 73:620-624, 2001.
Ando et al., Cancer Res., 60(24):6921-6926, 2000.

---

The invention claimed is:

1. A method for evaluating the risk of irinotecan toxicity in a cancer patient being considered for irinotecan therapy comprising:

obtaining a nucleic acid sample from the patient; and determining from the sample the nucleotide sequence at position −3156 in one or both UGT1A1 genes of the patient, wherein determination of an adenine residue at position −3156 in one or both UGT1A1 genes indicates the patient is at risk for irinotecan toxicity.

2. The method of claim 1, further comprising classifying the UGT1A1 activity level in the patient, whereby identification of a guanine residue indicates the patient does not have a low level of activity.

3. The method of claim 1, wherein the nucleotide sequence at position −3156 is determined for one UGT1A1 gene.

4. The method of claim 1, wherein the nucleotide sequence at position −3156 is determined for both UGT1A1 genes in the patient.

5. The method of claim 1, further comprising analyzing a glucuronidation rate associated with a sequence at position −3156 in one or both UGT1A1 genes.

6. The method of claim 1, further comprising optimizing a dose of irinotecan for administration to the patient.

7. The method according to claim 1, wherein determining the sequence at position −3156 in one or both UGT1A1 genes is performed by a hybridization assay.

8. The method according to claim 1, wherein determining the nucleotide sequence at position −3156 of a UGT1A1 gene or genes is performed by a sequencing or microsequencing assay.

9. The method according to claim 1, wherein determining the nucleotide sequence at position −3156 of a UGT1A1 gene or genes is performed by an allele-specific amplification assay.

10. The method of claim 1, further comprising administering to the patient irinotecan.

11. The method of claim 10, further comprising administering to the patient a second agent to reduce excretion of an active irinotecan species through the bile.

12. A method for evaluating the risk of irinotecan toxicity in a cancer patient being considered for irinotecan therapy comprising:

obtaining a nucleic acid sample from the patient; and, sequencing the sample to determine the nucleotide sequence at position −3156 in one or both UGT1A1 genes of the patient, wherein identification of an adenine residue at position −3156 in one or both UGT1A1 genes indicates the patient is at risk for irinotecan toxicity.

13. The method of claim 12, further comprising classifying the UGT1A1 activity level in the patient, whereby identification of a guanine residue indicates the patient does not have a low level of activity.

14. The method of claim 12, further comprising administering irinotecan to the patient if a guanine nucleotide is found at position −3156.

* * * * *

SEQUENCE LISTING

<160> NUMBER OF SEQ ID NOS: 14

<210> SEQ ID NO 1
<211> LENGTH: 261
<212> TYPE: DNA
<213> ORGANISM: Human immunodeficiency virus type 1

<400> SEQUENCE: 1

```
gcaaatctca cagacaatac taaaaccata atagtacagc tgaatcaatc tgtagaaatt      60
aattgcacaa gacccagcaa caatacaagg aaaagtatac atataggacc agggaaagca     120
ttttatgcaa caggaagcat aataggagat ataagacaag cacattgtaa ccttagtaga     180
acacaatgga ataacacttt agaacagata gttaaaaaat taagagaaca atttaaaaat     240
aaaacaatag cttttaagca c                                               261
```

<210> SEQ ID NO 2
<211> LENGTH: 20
<212> TYPE: DNA
<213> ORGANISM: Artificial Sequence
<220> FEATURE:
<223> OTHER INFORMATION: Synthetic Primer

<400> SEQUENCE: 2

```
gtcacgtgac acagtcaaac                                                  20
```

<210> SEQ ID NO 3
<211> LENGTH: 19
<212> TYPE: DNA
<213> ORGANISM: Artificial Sequence

```
<220> FEATURE:
<223> OTHER INFORMATION: Synthetic Primer

<400> SEQUENCE: 3
tttgctcctg ccagaggtt                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
ctggggataa acatgggatg                                                   20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
caccaccact tctggaacct                                                   20

<210> SEQ ID NO 6
<211> LENGTH: 22
<212> TYPE: DNA
<213> ORGANISM: Artificial Sequence
<220> FEATURE:
<223> OTHER INFORMATION: Synthetic Primer

<400> SEQUENCE: 6
acctctagtt acataacctg aa                                                22

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
aataaacccg acctcaccac                                                   20

<210> SEQ ID NO 8
<211> LENGTH: 19
<212> TYPE: DNA
<213> ORGANISM: Artificial Sequence
<220> FEATURE:
<223> OTHER INFORMATION: Synthetic Primer

<400> SEQUENCE: 8
gccaagggta gagttcagt                                                    19

<210> SEQ ID NO 9
<211> LENGTH: 18
<212> TYPE: DNA
<213> ORGANISM: Artificial Sequence
<220> FEATURE:
<223> OTHER INFORMATION: Synthetic Primer

<400> SEQUENCE: 9
gaccccagcc cacctgtc                                                     18
```

```
<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10
atgctgggaa gatactgttg                                                     20

<210> SEQ ID NO 11
<211> LENGTH: 20
<212> TYPE: DNA
<213> ORGANISM: Artificial Sequence
<220> FEATURE:
<223> OTHER INFORMATION: Synthetic Primer

<400> SEQUENCE: 11
tttggtgaag gcagttgatt                                                     20

<210> SEQ ID NO 12
<211> LENGTH: 22
<212> TYPE: DNA
<213> ORGANISM: Artificial Sequence
<220> FEATURE:
<223> OTHER INFORMATION: Synthetic Primer

<400> SEQUENCE: 12
gtcttcaagg tgtaaaatgc tc                                                  22

<210> SEQ ID NO 13
<211> LENGTH: 20
<212> TYPE: DNA
<213> ORGANISM: Artificial Sequence
<220> FEATURE:
<223> OTHER INFORMATION: Synthetic Primer

<400> SEQUENCE: 13
gtgcgacgtg gtttattccc                                                     20

<210> SEQ ID NO 14
<211> LENGTH: 472
<212> TYPE: DNA
<213> ORGANISM: Artificial Sequence
<220> FEATURE:
<223> OTHER INFORMATION: Synthetic Primer

<400> SEQUENCE: 14
tctcttcacc tcctccttat tctctttttg acactggatt ctttgctttg ataaattgtg         60
gggcaataca ctagtaaagg tcactcaatt ccaaggggaa aatgattaac caaagaacat        120
tctaacggtt cataaagggt attaggtgta atgaggatgt gttatctcac cagaacaaac        180
ttctgagttt atataacctc tagttacata acctgaaacc cggacttggc acttggtaag        240
cacgcaatga acagtcatag taagctggcc aagggtagag ttcagtttga acaaagcaat        300
ttgagaacat caaggaagt tggggaaca gcaggatc cagaatggct agagggtaag            360
aggcagaggg aggggcaag cagaagggct agagaggagg aatgagcttg acaggtggg          420 ctggggtcta tcccagagtt ttgagagcaa ggcagaggac tctgaatttt ct                472
```